United States Patent [19]
Colbert et al.

[11] Patent Number: 5,151,350
[45] Date of Patent: Sep. 29, 1992

[54] CLONED GENES ENCODING RECOMBINANT PROTEIN A

[75] Inventors: Donald A. Colbert, Bedford; Algis Anilionis, Arlington, both of Mass.

[73] Assignee: Repligen Corporation, Cambridge, Mass.

[21] Appl. No.: 436,955

[22] Filed: Oct. 27, 1982

[51] Int. Cl.$^5$ .................. C12P 21/02; C12N 15/11; C12N 15/31; C12N 15/00

[52] U.S. Cl. .................. 435/69.1; 435/172.3; 435/252.3; 435/252.33; 435/320.1; 536/27; 935/9; 935/11; 935/12

[58] Field of Search .................. 435/68, 70, 91, 71, 435/172, 253, 317, 172.3, 9, 11, 12, 320.1, 69.1, 69.3, 252.3–252.35; 536/27

[56] References Cited

U.S. PATENT DOCUMENTS

| | | | |
|---|---|---|---|
| 4,293,652 | 10/1981 | Cohen | 435/91 |
| 4,322,274 | 3/1982 | Wilson et al. | 204/182.9 |
| 4,338,397 | 7/1982 | Gilbert et al. | 435/70 |

OTHER PUBLICATIONS

Helling et al. in *Genetic Engineering*, Chakrabarty (ed.), CRC Press, 1978, pp. 1–30.
Broome et al: Proc. Natl. Acad. Sci. USA 75, 2746 (1976).
Maxam et al: Proc. Natl. Acad. Sci. USA 74, 560 (1977).
Itakura et al: Science 198, 1056 (1977).
Houghton et al: Nucl. Acids Res. 8, 2885 (1980).
Wallace et al: Nucleic Acids Res. 9: 879 (1981).
Bjork et al., Some Physicochemical Properties of Protein A from *Staph. aureus*, Eur. J. Biochem. 29, 579 (1972).
Sjodahl, Repetitive Sequences in Protein A from *Staph. aureus*, Eur. J. Biochem. 73, 343 (1977).
Sjodahl, Structural Studies on the Four Repetitive Fc–Binding Regions in Protein A, Eur. J. Biochem. 78, 471 (1977).
Barnes, Plasma Immunoabsorption: Alteration of Humoral Immune Components as a Treatment for Cancer, Cancer Bull. 33, 278 (1981).
Steele et al., Alteration of In Vitro Anti-Tumor Activity of Tumor-Bearer Sera by Absorption with *Staph. aureus*, Cowan I, Int. J. Cancer, 14, 83 (1974).
Sjodahl et al., The Fc Binding Regions in Protein A Are Not Responsible for the Polyclonal B Cell Activating Property of Protein A, Scand. J. Immunol., 10, 593 (1979).

*Primary Examiner*—James Martinell
*Attorney, Agent, or Firm*—Hamilton, Brook, Smith & Reynolds

[57] ABSTRACT

The gene coding for a protein A-like material has been successfully cloned and expressed for the first time. The cloning of this gene with its nucleotide sequence characterization, also disclosed, enables those skilled in the art to obtain quantities of a protein A-like material nucleotide sequence for cloning in various host-vector systems. Protein A is well known as a valuable component of a variety of diagnostic test systems. The protein A-like material of the subject invention, and subfragments thereof, have the protein A properties of binding to IgG at the Fc region and activation of polyclonal antibody synthesis. Thus, these entities are useful in the same manner as protein A.

45 Claims, No Drawings

CLONED GENES ENCODING RECOMBINANT PROTEIN A

BACKGROUND OF THE INVENTION

Protein A is a constituent of the cell wall of the bacterium *Staphylococcus aureus*. One form has a reported molecular weight of 42,000 and is a major component (1.7% of total cell protein) of the cell wall. See Bjork, (1972) *Eur. J. Biochem.* 29:579. Measurements of frictional ratio and intrinsic viscosity of protein A in comparison to most globular proteins suggest that its shape is relatively elongated. Controlled trypsinization of the molecule reveals 4 homologous peptide domains (designated in order from the N-terminus as D, A, B, C), each of which can bind one molecule of IgG at the Fc region. See Sjodahl, J. (1977) *Eur. J. Biochem.* 73:343 and L Sjodahl, J. (1977) *Eur. J. Biochem.* 78:471. The relative binding efficiency of protein A is dependent upon a number of factors, including pH, species, class, and subclass of IgG. Because of its ability to bind to IgG without significantly affecting the affinity of immunoglobulin for antigen, protein A is widely used as an immunoabsorbent in a variety of diagnostic and basic research test systems. See U.S. Pat. No. 4,322,274. Recent interest in applications of protein A has centered around its possible clinical use in anti-cancer treatment. Sensitized peripheral blood lymphocytes, normally responsible for cytotoxicity of tumor cells, are hypothesized to be inhibited in this function by serum blocking factors which are presumed to consist of specific antigens, antibodies, antiglobulins, and immune complexes. See Barnes, B. C. (1981) *Cancer Bull.* 33:278. These "blocking" factors can be removed from sera of tumor-bearers by absorption to *Staphlococcus aureus*, Cowan I cells which contain protein A, and thus allow cell-mediated tumor cell toxicity to proceed in in vitro test systems. See Steele, G., Ankerst, J., and Sjogren, H. (1974) *Int. J. Cancer* 14:83. Protein A also activates polyclonal antibody synthesis independent of its IgG binding activity. See Sjodahl, J. and Moller, G (1979) *Scand. J. Immunol.* 10:593.

Extensive testing of protein A as an anticancer agent has been inhibited by the high cost of the material and by the presence of impurities in some protein A preparations. Should the cost of protein A preparations be significantly reduced and the purity improved, then further clinical testing of protein A for anticancer uses would proceed more rapidly.

BRIEF SUMMARY OF THE INVENTION

Disclosed herein are recombinant plasmids comprising a novel nucleotide sequence coding for the amino acid sequence of protein A-like material and the well-known plasmid vector pBR322. The sequence of this novel oligonucleotide follows. The entire sequence is contained in plasmid pAC37. Plasmid pAC37-6 contains the same entire sequence except for the last 209 nucleotide bases. The last six nucleotide bases of pAC37-6 code for the PstI recognition sequence, i.e., CTGCAG.

The following sequence discloses for the first time, surprisingly, an additional IgG-binding domain designated domain E near the amino terminal end of the protein A-like material. This domain is neither disclosed nor suggested by the prior art. In addition, an unexpectedly large carboxy terminal coding sequence has been discovered, which may constitute the region responsible for activation of polyclonal antibody synthesis.

The disclosed nucleotide sequence and fragments thereof enable persons in the art, for the first time, to obtain cloned nucleotide sequences coding for protein A-like material and fragments of protein A-like material.

```
TTG AAA AAG AAA AAC ATT TAT TCA ATT CGT AAA CTA GGT GTA GGT ATT GCA TCT GTA ACT TTA GGT
Met Lys Lys Lys Asn Ile Tyr Ser Ile Arg Lys Leu Gly Val Gly Ile Ala Ser Val Thr Leu Gly

ACA TTA CTT ATA TCT GGT GGC GTA ACA CCT GCT GCA AAT GCT GCG CAA CAC GAT GAA GCT CAA CAA
Thr Leu Leu Ile Ser Gly Gly Val Thr Pro Ala Ala Asn Ala Ala Gln His Asp Glu Ala Gln Gln
```
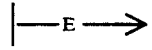

```
AAT GCT TTT TAT CAA GTG TTA AAT ATG CCT AAC TTA AAC GCT GAT CAA CGT AAT GGT TTT ATC CAA
Asn Ala Phe Tyr Gln Val Leu Asn Met Pro Asn Leu Asn Ala Asp Gln Arg Asn Gly Phe Ile Gln

AGC TTT AAA GAT GAT CCA AGC CAA AGT GCT AAC GTT TTA GGT GAA GCT CAA AAA CTT AAT GAC TCT
Ser Leu Lys Asp Asp Pro Ser Gln Ser Ala Asn Val Leu Gly Glu Ala Gln Lys Leu Asn Asp Ser

CAA GCT CCA AAA GCT GAT GCG CAA CAA AAT AAG TTC AAC AAA GAT CAA CAA AGC GCC TTC TAT GAA
Gln Ala Pro Lys Ala Asp Ala Gln Gln Asn Lys Phe Asn Lys Asp Gln Gln Ser Ala Phe Tyr Glu
```
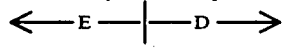

```
ATC TTG AAC ATG CCT AAC TTA AAC GAG GAG CAA CGC AAT GGT TTC ATT CAA AGT CTT AAA GAC GAT
Ile Leu Asn Met Pro Asn Leu Asn Glu Glu Gln Arg Asn Gly Phe Ile Gln Ser Leu Lys Asp Asp

CCA AGC CAA AGC ACT AAC GTT TTA GGT GAA GCT AAA AAA TTA AAC GAA TCT CAA GCA CCG AAA GCT
Pro Ser Gln Ser Thr Asn Val Leu Gly Glu Ala Lys Lys Leu Asn Glu Ser Gln Ala Pro Lys Ala
```

```
GAC AAC AAT TTC AAC AAA GAA CAA CAA AAT GCT TTC TAT GAA ATC TTG AAC ATG CCT AAC TTG AAC
Asp Asn Asn Phe Asn Lys Glu Gln Gln Asn Ala Phe Tyr Glu Ile Leu Asn Met Pro Asn Leu Asn

GAA GAA CAA CGC AAT GGT TTC ATC CAA AGC TTA AAA GAT GAC CCA AGT CAA AGT GCT AAC CTT TTA
Glu Glu Gln Arg Asn Gly Phe Ile Gln Ser Leu Lys Asp Asp Pro Ser Gln Ser Ala Asn Leu Leu
```

-continued

```
GCA GAA GCT AAA AAG TTA AAT GAA TCT CAA GCA CCG AAA GCT GAT AAC AAA TTC AAC AAA GAA CAA
Ala Glu Ala Lys Lys Leu Asn Glu Ser Gln Ala Pro Lys Ala Asp Asn Lys Phe Asn Lys Glu Gln
                                        <— A —|— B —>

CAA AAT GCT TTC TAT GAA ATC TTA CAT TTA CCT AAC TTA AAT GAA GAA CAA CGC AAT GGT TTC ATC
Gln Asn Ala Phe Tyr Glu Ile Leu His Leu Pro Asn Leu Asn Glu Glu Gln Arg Asn Gly Phe Ile

CAA AGC TTA AAA GAT GAC CCA AGC CAA AGC GCT AAC CTT TTA GCA GAA GCT AAA AAG CTA AAT GAT
Gln Ser Leu Lys Asp Asp Pro Ser Gln Ser Ala Asn Leu Leu Ala Glu Ala Lys Lys Leu Asn Asp

GCA CAA GCA CCA AAA GCT GAC AAC AAA TTC AAC AAA GAA CAA CAA AAT GCT TTC TAT GAA ATT TTA
Ala Gln Ala Pro Lys Ala Asp Asn Lys Phe Asn Lys Glu Gln Gln Asn Ala Phe Tyr Glu Ile Leu
    <— B —|— C —>

CAT TTA CCT AAC TTA ACT GAA GAA CAA CGT AAC GGC TTC ATC CAA AGC CTT AAA GAC GAT CCT TCA
His Leu Pro Asn Leu Thr Glu Glu Gln Arg Asn Gly Phe Ile Gln Ser Leu Lys Asp Asp Pro Ser

GTG AGC AAA GAA ATT TTA GCA GAA GCT AAA AAG CTA AAC GAT GCT CAA GCA CCA AAA GAG GAA GAC
Val Ser Lys Glu Ile Leu Ala Glu Ala Lys Lys Leu Asn Asp Ala Gln Ala Pro Lys Glu Glu Asp
                                                                     <— C —|

AAC AAC AAG CCT GGT AAA GAA GAC GGC AAC AAA CCT GGT AAA GAA GAC GGC AAC AAA CCT GGT AAA
Asn Asn Lys Pro Gly Lys Glu Asp Gly Asn Lys Pro Gly Lys Glu Asp Gly Asn Lys Pro Gly Lys

GAA GAC AAC AAA AAC CTT GGC AAA GAA GAC GGC AAC AAA CCT GGT AAA GAA GAC AAC AAA AAA CCT
Glu Asp Asn Lys Asn Leu Gly Lys Glu Asp Gly Asn Lys Pro Gly Lys Glu Asp Asn Lys Lys Pro

GGC AAA GAA GAT GGC AAC AAA CCT GGT AAA GAA GAC GGC AAC AAG CCT GGT AAA GAA GAT GGC AAC
Gly Lys Glu Asp Gly Asn Lys Pro Gly Lys Glu Asp Gly Asn Lys Pro Gly Lys Glu Asp Gly Asn

AAA CCT GCT AAA GAA GAT GGC AAC AAG CCT GGT AAA GAA GAT GGC AAC AAG CCT CGT AAA GAA GAC
Lys Pro Gly Lys Glu Asp Gly Asn Lys Pro Gly Lys Glu Asp Gly Asn Lys Pro Gly Lys Glu Asp

GGC AAC GGA GTA CAT GTC GTT AAA CCT GGT GAT ACA GTA AAT GAC ATT GCA AAA GCA AAC GGC ACT
Gly Asn Gly Val His Val Val Lys Pro Gly Asp Thr Val Asn Asp Ile Ala Lys Ala Asn Gly Thr

ACT GCT GAC AAA ATT GCT GCA GAT AAC AAA TTA GCT GAT AAA AAC ATG ATC AAA CCT GGT CAA GAA
Thr Ala Asp Lys Ile Ala Ala Asp Asn Lys Leu Ala Asp Lys Asn Met Ile Lys Pro Gly Gln Glu

CTT GTT GTT GAT AAG AAG CAA CCA GCA AAC CAT GCA GAT GCT AAC AAA GCT CAA GCA TTA CCA GAA
Leu Val Val Asp Lys Lys Gln Pro Ala Asn His Ala Asp Ala Asn Lys Ala Gln Ala Leu Pro Glu

ACT GGT GAA GAA AAT CCA TTC ATC GGT ACA ACT GTA TTT GGT GGA TTA TCA TTA GCG TTA GGT GCA
Thr Gly Glu Glu Asn Pro Leu Ile Gly Thr Thr Val Phe Gly Gly Leu Ser Leu Ala Leu Gly Ala

GCG TTA TTA GCT GGA CGT CGT CGC GAA CTA TAA
Ala Leu Leu Ala Gly Arg Arg Arg Glu Leu Stop
```

Having the above data, those skilled in the art can readily appreciate the identity of other equivalent nucleotide sequences coding for molecules with substantially the same protein A-like biological activity. Thus, the scope of the subject invention includes not only the specific nucleotide sequence depicted above, but also all equivalent nucleotide sequences coding for molecules with substantially the same protein A-like biological activity. The term "equivalent" is being used in its ordinary patent usage here as denoting a nucleotide sequence which performs substantially as the nucleotide sequence identified herein to produce molecules with substantially the same protein A-like biological activity in essentially the same kind of hosts. Within this definition are fragments of the protein A-like material which have the property of binding to IgG at the Fc region, or fragments which have polyclonal B-cell activating activity. The protein A-like material of the subject invention, and fragments thereof, can be used in the same manner as protein A, disclosed above.

DETAILED DESCRIPTION OF THE INVENTION

Cloning of the DNA sequences coding for protein A-like material was initiated by construction of a gene bank comprising DNA sequences of the SAC genome (*S. aureus*, Cowan I, SAC, ATCC 12598). This was accomplished by G-C tailing using blunt-end SAC DNA fragments generated by HaeIII+AluI partial restriction digestion as substrate. Digestion of 250 μg SAC DNA in 400 μl 50 mM Tris-HCl, pH 7.5: 5 mM MgCl: 1 mM dithiothreitol (DTT) with 150 units HaeIII and 200 units AluI (12 min., 37° C.) generated a broad size range of DNA fragments (2-10 kilobase pairs [kb]). From the published 42,000 molecular weight, it was estimated that the coding sequences of protein A should comprise 1.1-1.2 kb of DNA. To maximize the probability of obtaining a recombinant insert containing both the protein A coding sequences and adjacent regulatory sequences, larger fragments, 3-6 kb, were used for construction of the SAC gene bank. This DNA was extracted from a preparative agarose gel, tailed with 15°-20° C. residues with terminal transferase, and annealed to G-tailed, PstI-digested pBR322. Transformation of *E. coli* MS371 cells with the resulting recombinant DNA, G-tailed plasmid DNA alone, or uncut pBR322 yielded transformation efficiencies of $2.0\times10^4$, $5.0\times10^2$, and $2.0\times10^6$ transformants per 72 g plasmid DNA, respectively. Approximately $7.0\times10^3$ transformants were picked onto fresh tetracycline plates for screening.

Mini-lysate plasmid DNA preparations for 10 randomly picked transformants were digested with PstI and the sizes of the resulting DNA fragments analyzed by agarose gel electrophoresis. The results indicated that (1) 9 of 10 transformants carried recombinant DNA plasmids, (2) 7 of 9 recombinant plasmids had both PstI restriction sites regenerated by the G-C tailing procedure, and (3) the average insert length was approximately 3.0 kb.

The cloning vehicles of the subject invention are useful to make available for the first time and to increase the supply of the gene coding for molecules with protein A-like biological activity by replication of a transformed host. With this abundance of the desired gene, levels of protein A expression necessary to make protein A-like material available at a lower cost can be predicted.

Following are examples which illustrate procedures, including the best mode, for practicing the invention. These examples should not be construed as limiting. All percentages are by weight and all solvent mixture proportions are by volume unless otherwise noted.

EXAMPLE 1

MAINTENANCE AND GROWTH OF BACTERIAL STRAINS

*Staphylococcus aureus,* Cowan I (SAC, ATCC 12598) and Woods 46 (SAW, ATCC 10832) strains were obtained from the American Type Culture Collection, Rockville, Md., Both strains were grown (liquid or 1.5% agar plates) in Penassay medium (5 mg/ml Casitone, 2.5 mg/ml yeast extract, 2.5 mg/ml β-glycerophosphate, 4 mg/ml niacin, 2 mg/ml thiamine-HCl) under standard conditions.

*E. coli* MS371 was propagated in L-broth (5 g/l NaCl, 10 g/l bactotryptone, 5 g/l yeast extract). For plasmid DNA preparation, cells containing plasmids of interest were grown in M-9 media (49 mM $Na_2HPO_4$, 17 mM $KH_2PO_4$, 8.6 mM NaCl, 18.7 mM $NH_4Cl$, 0.1 mM $CaCl_2$, 1 mM $MgSO_4$. 7 $H_2O$, 0.4% glucose, 0.4% casamino acids, 2 mg/ml thiamine).

EXAMPLE 2

EXTRACTION OF DNA FROM SAC

Overnight cultures of SAC were diluted 1:100 with Penassay broth and allowed to grow to $OD_{600}=0.6$. The cells were pelleted by centrifugation (5K rpm, 10 min., 2° C. with a Beckman JA10 rotor), resuspended in 20 volumes DNA extraction buffer (0.1 M NaCl; 50 mM EDTA; 10 mM Tris-HCl, pH 8.0), and frozen in a dry ice-acetone bath.

The frozen cell suspension was allowed to thaw at 37° C., 50 mg/ml lysostaphin (Sigma Chemical Co., St. Louis, Mo.) was added, and the suspension incubated at 37° C., 15 min. Protease K (40 mg/ml) and SDS (0.5%) were added and the mixture incubated at 37° C., 1 hour. The lysate was then extracted with phenol:chloroform (1:1) saturated with DNA extraction buffer. The SAC DNA solution was adjusted to 0.95 g/ml CsCl and banded by centrifugation (44 K rpm, 48 hours, 23° C. with a Beckman Ti60 rotor). The DNA was then harvested with a syringe and 21 g needle by side puncture. The DNA was dialyzed against TE buffer (10 mM Tris-HCl; 1 mM EDTA, pH 8.0), phenol:chloroform-extracted as before, and precipitated twice with 2 volumes ethanol. Yields of SAC DNA ranged between 700-800 mg DNA per gram wet weight of cells.

EXAMPLE 3

RESTRICTION ENZYME DIGESTION

All restriction endonucleases were purchased from Bethesda Research Laboratories, Bethesda, Md. or New England Biolabs, Beverly, Mass. Unless otherwise indicated, restriction digests, described herein, were carried out at DNA concentrations of 100–400 μg/ml, 2–4 units enzyme per μg DNA, 2–3 hours, 37° C., in buffer systems recommended for each enzyme by the respective company.

EXAMPLE 4

ELECTROPHORESIS AND EXTRACTION OF DNA FRAGMENTS

Agarose gel electrophoresis was carried out using a 2×Tris-acetate gel buffer (80 mM Tris-HCl, pH 8.0., 40 mM $NaC_2H_3O_2$; 36 mM NaCl; 2 mM $Na_2EDTA$) in the gel and 1× buffer for the run. Analytical gels were routinely run as "submarine gels" in a horizontal gel box. Preparative gels were routinely run in an EC Model 470 gel box. DNA bands were visualized by ethidium bromide (EtBr) post-staining (0.5 mg/ml in 1×gel buffer) and use of a U.V. transilluminator Model TM-36 from Ultra-Violet Products, Inc., San Gabriel, Ca.

Extraction of DNA from preparative agarose gels was initiated by visualization of the positions of EtBr-stained bands of a single gel lane. Gel slices containing DNA fragments of interest were diced manually and passed through a 20 g needle with 1½–2 volumes DNA gel extraction buffer (0.5 M $NH_4C_2H_3O_2$, 10 mM EDTA, 10 mM $Mg(C_2H_3O_2)_2$, 0.1% SDS). An equal volume of phenol saturated with 1 mM $NH_4C_2H_3O_2$, 10 mM EDTA was added and extraction carried out in Eppendorf tubes) (trademark of Brinkman Instruments) on a rotary shaker at 23° C. overnight. The tubes were then placed on ice for 30 min. prior to separation of the aqueous phase by microcentrifugation. Extraction of the aqueous phase with the saturated phenol solution was repeated 3–4 times, followed by chloroform extraction and ethanol precipitation. Routine recovery of DNA fragments smaller than 15 kb was about 40%.

EXAMPLE 5

TAILING AND ANNEALING OF PLASMID AND Insert DNA

Construction of recombinant plasmids was facilitated by G-C tailing (Stein, I., Catterall, J., Woo, S., Means, A., O'Malley, B. [1978]*Biochemistry.* 17:5763). PstI-digested and agarose gel-purified pBR322 DNA was tailed with approximately 14 G residues in a 100 μl reaction under the following conditions: 100 μg/ml DNA, 20 μM dGTP, 200 mM K/cacodylate, 1 mM $CoCl_2$, 1 mM β-mercaptoethanol (B-SH), 15 units terminal deoxynucleotidyl transferase (P. L. Biochemicals, Inc., Milwaukee, Wis.) 37° C., 30 min. The reaction was terminated by the addition of 2 μl 100 mM EDTA, 2 μl 5 M NaCl, 2 μl 20% SDS and phenol:chloroform (1:1) extraction. The resulting G-tailed plasmid DNA was passed over a G-50 Sephadex column and precipitated with ethanol.

Target SAC DNA fragments of average 3–5 kb length were tailed with 15°–20° C. residues in a 30 μl reaction under the following conditions: 4–5 µg SAC DNA, 20 µM dCTP, 200 mM K/cacodylate, 1 mM CoCl₂, 1 mM β-SH, 4.5 units terminal deoxynucleotidyl transferase: 37° C., 12 min. Termination of the reaction and treatment of C-tailed SAC DNA was carried out as described above. Annealing of plasmid and target SAC DNA was initiated by mixing 2.5 µg plasmid and 4.0 µg target SAC DNA in 300 µl 10 mM Tris-HCl,pH 8.0; 1 mM EDTA., 100 mM NaCl; and heating for 10 min. at 68° C. The annealing solution was then allowed to incubate 1 hour at 55° C., 1 hour at 23° C., and was stored at 4° C. until needed.

EXAMPLE 6

LIGATION OF DNA FRAGMENTS

Ligation of staggered-end DNA fragments was carried out with 100–200 units/ml T₄ DNA ligase (Bethesda Research Laboratories); 66 µM ATP; 66 mM Tris-HCl, pH 7.6; 6.6 mM MgCl₂; 10 mM dithiothreitol; at 12° C., 12–16 hours.

EXAMPLE 7

Transformation OF E. COLI MS371 Cells

Fresh overnight cultures were diluted 1:100 in L-broth and allowed to grow at 37° C. with shaking to $OD_{600=0.1-0.15}$. The cells were pelleted (5 min. 5K rpm, 5° C. in a JA20 rotor in a Beckman J2-20 centrifuge), resuspended in half the original volume of ice-cold 50 mM MnCl₂; 10 mM NaC pH 5.6; and allowed to stand at 0° C., 20 min. Following pelleting of the cells as above, they were resuspended in ice-cold 100 mM MnCl₂; 75 mM CaCl₂; 10 mM NaC₂H₃O₂, pH 5.6. A 0.1 ml aliquot of cells was mixed with 10 µl DNA transformation solution and allowed to sit on ice 40 min. The cells were then subjected to heat shock (2.5 min., 25°–30° C.) and 1.5 µl 2.0 M Tris-HCl, pH 7.4,and 0.5 ml L-broth per 0.1 ml cell aliquot were added. The cells were then plated in 15–25 µl aliquots on 1.5% agar L-broth plates supplemented with 10 µg/ml tetracycline (Sigma) and incubated overnight at 37° C. Transformation efficiencies of $1.0 \times 10^7$ colonies per µg pBR322 DNA were routinely observed.

EXAMPLE 8

MINI-LYSATE PLASMID DNA PREPARATIONS

Mini-lysate plasmid preparation was initiated by addition of 1 ml of fresh overnight culture to 9 ml L-broth, supplemented with 1% glucose and allowed to grow with shaking at 37° C. to an $OD_{550}$ of 1.0. Chloramphenicol was then added to 150 µg/ml and the culture incubated for 12–16 hours at 37° C. The cells were then pelleted by centrifugation (5 min., 3K rpm, 23° C. in an RC-3 centrifuge), resuspended in ice-cold TE buffer, and transferred to a 1.5 ml eppendorf tube to be repelleted by centrifugation. The resulting cell pellet was resuspended in 50 mM Tris-HCl.pH 8.0; 50 mM EDTA; 15% sucrose (wt/vol) by vortexing. To the cell suspension, 10 µl of 10% SDS were added and incubated at 70° C., 10 min. To the resulting lysate, 62.5 µl ice-cold 4 M potassium acetate was added and the lysate allowed to stand for at least 2 hours on ice. Following centrifugation the supernatant volume was adjusted to 0.5 ml with H₂O and the DNA precipitated with 2 volumes absolute ethanol. The DNA was then resuspended in 100 µl TE, the salt adjusted to 0.1 M with NaCl, and re-precipitated with two volumes ethanol prior to restriction enzyme analysis.

EXAMPLE 9

LARGE-SCALE PLASMID DNA PREPARATIONS

Overnight 25 ml cultures were grown in L-broth supplemented with 10 µg/ml tetracycline. To one liter M-9 media, 5 ml of the overnight culture were added and allowed to grow at 37° C. in a rotary incubator (200 rpm) until an $OD_{600}$ value of 0.6 was reached. 250 mg/liter chloramphenicol (Sigma) was then added and the culture allowed to shake for 12–16 hours at 37° C. The cells were then harvested by centrifugation (6000 rpm, 20 min., 2° C. in Beckman JA-10 rotor), and the pellets washed once with ice-cold TE buffer. The washed pellets were then either frozen at −60° C. or immediately extracted. Preparation of cleared lysates was initiated by suspending the cell pellet in 6.25 ml per liter original culture of 25% sucrose in 50 mM Tris-HCl, pH 8.0, and then adding 1.5 ml of a freshly made 10 mg/ml lysozyme (Sigma) solution. After continuous swirling of the suspension on ice for 5 min., 1 25 ml of 0.5 M Na₂EDTA, pH 8.0, was added and swirling of the suspension on ice continued for 5 min. Ten ml of a 10×Triton (10 ml 10% Triton X-100; 125 ml 0.5 M EDTA, pH 8.0; 50 ml 1.0 M Tris-HCl; pH 8.0: and 800 ml H₂O) per liter original culture volume was added and the suspension swirled on ice for 15 min. The lysate was then subjected to centrifugation (19 K rpm, 4° C., 30 min. in a JA-20 rotor) and the supernatant transferred to a volumetric cylinder. 0.95 g/ml CsCl was dissolved in the supernatant and 1/10 the volume of 10 mg/ml EtBr in TE buffer was added. Separation of plasmid and chromosomal DNA was accomplished by centrifugation with a Beckman Ti 50.2 rotor (23° C., 44K rpm for 24 hours followed by 36 hours at 38 K rpm).

The plasmid DNA band on the gradient is visualized with a U.V. lamp and harvested with a syringe by side puncture using a 21 g needle. Removal of EtBr is carried out by repeated isobutyl alcohol extraction. The plasmid solution is then dialyzed overnight against TE buffer, the salt concentration adjusted to 0.1 M NaCl and precipitation of DNA carried out with 2 volumes of absolute ethanol.

EXAMPLE 10

¹²⁵I-IGG-PROTEIN A BINDING ASSAY

Expression of protein A-like activity in bacterial colonies was detected by binding of 125I-IgG to colony lysates immobilized on nitrocellulose filters. Recombinant plasmid-bearing E. coli, SAC (positive control) and SAW (negative control) cells were picked and streaked onto nutrient agar plates and allowed to grow overnight. Nitrocellulose filter discs (BA85, 87 mm, Schleicher and Schuell, Keene, N. H.) were carefully laid on the plates to absorb the underlying colonies, and the filters lifted and allowed to dry by blotting on Whatman 3 MM paper. Lysis of filter-bound cells was accomplished by laying the filters (colony side up) on sheets of Whatman 3MM filter paper saturated with 0.5 M NaOH and allowing lysis to proceed for 10 min. at 23° C. Following lysis, the filters were blot dried and neutralized on filter paper saturated with 1.0 M Tris-HCl, pH 7.0. The filters were again blot dried and pretreated with protein binding solution (10 mM Tris-HCl, pH 7.0; 100 mM NaCl; 5 mM EDTA; 0.13% NP40; 0.1% SDS: 0.1% sodium deoxycholate: 0.2% Ficoll 400; 0.3% gelatin) for 4-6 hours at 23° C. on a rotary platform shaker. After pre-treatment, the filters were transferred to a 1-liter beaker containing a 4.5 ml/filter protein-binding solution. Binding of $^{125}$I-IgG (Goat Anti-rabbit, New England Nuclear, Boston, Mass.) was carried out by the addition of $5 \times 10^6$ cpm/ml $^{125}$I-IgG to the beaker and allowing binding to occur at 4° C. overnight with constant rotary shaking. Washing of the filters was accomplished by repeated washing with 500 ml protein-binding solutions: the first wash carried out at 4° C., and 2-3 additional washes carried out at 23° C. The washed filters were then dried by blotting and detection of $^{125}$I-IgG binding accomplished by radioautography, using Kodak XAR-5 film and two DuPont Cronex Lightning-Plus enhancement screens.

EXAMPLE 11

DNA SEQUENCING

DNA sequence determination was carried out with minor modification of procedures described by Maxam and Gilbert (Maxam, A. and Gilbert, W. [1977]Proc. Nat'l. Acad. Sci. USA, 74:560) and Heidecker et al. (Heidecker, G., Messing, J., and Gronenborn, B. [1980]Gene 10:69).

EXAMPLE 12

SCREENING FOR EXPRESSION OF PROTEIN A-LIKE Material in E. coli Transformants To test for the expression of sequences coding for protein A-like material within the recombinant SAC gene bank, the colonies from 50 plates of 52 colonies each (2,600) were lifted on nitrocellulose discs and assayed for $^{125}$I-IgG binding. Filters containing SAC and SAW colonies were included in the assay as positive and negative controls, respectively. To assess the sensitivity of the assay, serial dilutions of purified protein A (Pharmacia, Piscataway, N.J.) were spotted onto a nitrocellulose disc and assayed in parallel with the test filters. The routine sensitivity for the assay was found to vary over a range of 1.0 to 0.01 ng with purified protein A. Filters containing SAC and SAW cells yielded positive and negative autoradiographic signals, respectively. A single transformant colony bound significant $^{125}$I-IgG in this and subsequent assays. This colony was picked for further analysis. The plasmid contained in this colony was designated pAc37.

EXAMPLE 13

DETERMINATION OF THE PROTEIN A-LIKE GENE Domain Within the pAc37 Insert

Restriction endonuclease analysis of pAc37 plasmid DNA indicated the presence of PstI insert fragments of 3.1, 2.3, 1.9, and 0.65 kb length. pAc37 plasmid DNA was digested with PstI, re-ligated with T4 ligase, and used to transform E. coli MS371 cells. The resulting transformants were screened by the $^{125}$I-IgG-binding assay as described in example 12.

Of 322 transformants, 10 positive $^{125}$I-IgG-binding colonies were obtained and were found to have recombinant plasmids containing a 1.9 kb PstI insert. When recombinant plasmid DNAs from 12 randomly picked non-$^{125}$I-IgG-binding transformant colonies were analyzed they were found to contain one or more PstI fragments from pAc37, but not a 1.9 kb fragment. It was concluded that at least a portion of the protein A-like coding sequences reside within a 1.9 kb PstI fragment of pAc37. One positive colony containing a recombinant plasmid with a single 1.9 kb insert, designated pAc37-6, was picked for further analysis.

EXAMPLE 14

IDENTIFICATION OF THE PROTEIN A-LIKE CODING Sequences Within pAc37-6 DNA

Final determination of the presence of protein A-like coding sequences within the PstI 1.9 kb fragment of pAc37-6 DNA was accomplished by DNA sequence determination. The pAc37-6 DNA was digested with HindIII, labeled with $\gamma^{32}$P-ATP and polynucleotide kinase, and subsequently digested with PstI. Sequence determination of a portion of the 0.6 kb HindIII/PstI fragment indicated sequence colinearity with the known amino acid sequence of the B-C junction of the protein A molecule. The position of the sequences coding for the B-C junction of the protein A-like material within the insert made it likely that the 1.9 kb insert of pAc37-6 plasmid DNA contained most of the sequences coding for the protein A gene, including the ribosome binding site, and 5' regulatory sequences.

EXAMPLE 15

PURIFICATION OF PROTEIN A-LIKE MATERIAL FROM E. coli MS371 (pAc37-6), NRRL B-15131

E. coli MS371 (pAc37-6) is lysed with 0.1 N NaOH and centrifuged. The supernatant is removed and 25 mM monobasic sodium phosphate is added and the solution adjusted to pH 7.0 with 1 M HCl. The protein solution is dialyzed against 25 mM sodium phosphate pH 7.0, then clarified by centrifugation.

The solution is applied to an IgG-Sepharose column (30 ml bed volume per 1.3 gm of protein) and the column washed with 0.1 M sodium phosphate pH 7.0 until no protein, as determined by $A_{280}$, elutes from the column.

Protein A-like material is eluted with 0.1 M glycine.HCl. The purified protein is concentrated by precipitation with 80% saturated $(NH_4)_2SO_4$, dialyzed versus 10 mM sodium phosphate pH 7.0, and stored frozen.

The purification of protein A-like material from E. coli MS371 (pAc37), NRRL B-15127 can be accomplished by using the procedure described above.

EXAMPLE 16

ISOLATION OF NUCLEOTIDE SEQUENCES CODING for fragments of the Amino Acid Sequence Coding for Protein A-Like Material from E. coli MS371 (pAc37-6), NRRL B-15131

Restriction enzymes can be used to cleave the nucleotide sequence coding for protein A-like material in order to isolate essentially pure fragments of the coding region that are capable of coding for amino acid sequences with biological activities similar to those of protein A. For example, cleavage of pAc37-6 DNA with RsaI restriction endonuclease will yield an oligonucleotide that is 1,199 nucleotides long and that codes for a polypeptide containing domains E, D, A, B, and C. Digestion with other restriction enzymes such as HinfI, or a combination of enzymes such as HindIII and Sau3A, can be used to generate essentially pure, well-defined oligonucleotide fragments that code for amino acid sequences with biological activities similar to those of protein A.

The desired oligonucleotide fragments are isolated in their essentially pure form by preparative agarose gel electrophoresis as follows: Agarose is dissolved to 1% in 2x E buffer (0.08 M Tris.HCl, pH 7.8; 0.01 M NaC$_2$H$_3$O$_2$; 0.002 M EDTA) and poured into a Bio-Rad (Richmond, Ca.) slab gel apparatus. Samples are dissolved in 10 mM Tris.HCl, pH 8.0; 0.1 mM EDTA and the samples are run at constant power with 2×E running buffer.

After electrophoresis, one lane is cut from the gel, stained with ethidium bromide (0.5 μgm/ml) and the DNA bands visualized under ultraviolet light. The band of interest is cut from the rest of the gel and macerated before passing it through a 20 guage needle. An equal weight of extraction buffer (10 mM Tris.HCl, pH 8.0; 2 mM EDTA: 1 M NaCl) is then added and mixed with the gel. The mixture is incubated at 47° C. for 16 hours and the agarose pelleted at 100,000×g for 1 hour. The supernatant is then made 30 μgm/ml in tRNA and extracted with phenol until no agarose is visible at the interface. The DNA is then ether extracted and ethanol precipitated. Gel buffers and extraction procedures can be varied by one skilled in the art to recover the desired DNA fragments.

EXAMPLE 17

SYNTHESIS OF NUCLEOTIDE SEQUENCES CODING for the Amino Acid Sequences of Domains E, D, A, B, and C of Protein A-Like Material Once the nucleotide sequence coding for a particular amino acid sequence has been determined, i.e., by cloning and sequencing as shown in previous examples, then the oligonucleotide coding for the amino acid sequence can be synthesized chemically. (See, for example, Edge, M. D., et al. [1981]*Nature* 292:756-762.) Thus, fragments of the coding region, or the entire coding region for a protein A-like molecule, can be synthesized and isolated in their essentially pure forms; this includes those regions of the coding sequence coding for domains E, D, A, B, and C.

Domains E, D, A, B, and C, each alone, or in various combinations, are useful in the same manner as protein A to bind IgG in diagnostic test systems, as described previously.

EXAMPLE 18

Cloning and Expression of the Nucleotide Sequences Coding for the Amino Acid Sequences of Domains E, D, A, B, and C of Protein A-Like Material The essentially pure nucleotide sequences coding for protein A-like material or for biologically active fragments of protein A-like material, isolated and synthesized as described in examples 16 and 17, respectively, can be ligated into appropriate restriction enzyme sites in an expression cloning vector. If necessary, sites can be added to nucleotide sequences using linker molecules. (See, for example, Norris, K. E., et al. [1979]*Gene* 7:355-362.) The ligated DNA can then be used to transform a host organism. Previous work by others has shown that expression of the cloned nucleotide sequence would be expected. (See, for example, Doel, M. T. et al. [1980]*Nuc. Acids Res.* 8: 4575-4592: Roberts T., et al. [1979]*Proc. Nat. Acad. Sci.* 76:760-764; Guarente, L., et al. [1980]*Cell* 20: 543-553.) The biologically active material that is expressed can then be purified as described in example 15.

Plasmids pAc37 and pAc37-6 have been deposited in an *E. coli* host in the permanent collection of the Northern Regional Research Laboratory (NRRL), U.S. Department of Agriculture, Peoria, Ill., U.S.A. Their accession numbers in this repository are as follows:

*E. coli* MS371 (pAc37)--NRRL B-15127: Deposited on Aug. 18, 1982

*E. coli* MS371 (pAc37-6)--NRRL B-15131: Deposited on Aug. 18, 1982

*E. coli* MS371--NRRL B-15129: Deposited on Aug. 18, 1982

Plasmid pBR322 is a well-known and available plasmid. It is maintained in the *E. coli* host ATCC 37017. Purified pBR322 DNA can be obtained as described in Bolivar, F., Rodriquez, R. L., Greene, P. J., Betlach, M. C., Heyneker, H. L., Boyer, H. W., Crosa, J. H., and Falkow, S. (1977) *Gene* 2:95-113; and Sutcliffe, J. G. (1978) *Nucleic Acids Res.* 5:2721-2728.

NRRL B-15127, NRRL B-15131, and NRRL B-15129, are available to the public upon the grant of a patent which discloses these accession numbers in conjunction with the invention described herein. It should be understood that the availability of these deposits does not constitute a license to practice the subject invention in derogation of patent rights granted for the subject invention by governmental action.

There are other well-known hosts which can be used instead of *E. coli* MS371, for example, *B. subtilis, Streptomyces* species, and yeast.

Also, it is within the skill of those in the art to vary the conditions required to grow cells, extract DNA, perform restriction enzyme digestions, electrophorese DNA fragments, tail and anneal plasmid and insert DNA, ligate DNA, transform *E. coli* cells, prepare plasmid DNA, perform an IgG-binding assay, prepare protein lysates, electrophorese proteins, and sequence DNA.

We claim:

1. A microorganism comprising a recombinant plasmid containing a nucleotide sequence coding for the amino acid sequence of a protein A material having a protein A biological activity, and equivalent nucleotide sequences coding for molecules with substantially the same protein A-like biological activity, said nucleotide sequence and said amino acid sequence are as follows:

```
TTG AAA AAG AAA AAC ATT TAT TCA ATT CGT AAA
Met Lys Lys Lys Asn Ile Tyr Ser Ile Arg Lys

CTA GGT GTA GGT ATT GCA TCT GTA ACT TTA GGT
Leu Gly Val Gly Ile Ala Ser Val Thr Leu Gly

ACA TTA CTT ATA TCT GGT GGC GTA ACA CCT GCT
Thr Leu Leu Ile Ser Gly Gly Val Thr Pro Ala

GCA AAT GCT GCG CAA CAC GAT GAA GCT CAA CAA
Ala Asn Ala Ala Gln His Asp Glu Ala Gln Gln
                                |—E—>

AAT GCT TTT TAT CAA GTG TTA AAT ATG CCT AAC
Asn Ala Phe Tyr Gln Val Leu Asn Met Pro Asn

TTA AAC GCT GAT CAA CGT AAT GGT TTT ATC CAA
Leu Asn Ala Asp Gln Arg Asn Gly Phe Ile Gln

AGC CTT AAA GAT GAT CCA AGC CAA AGT GCT AAC
Ser Leu Lys Asp Asp Pro Ser Gln Ser Ala Asn
```

-continued

```
GTT TTA GGT GAA GCT CAA AAA CTT AAT GAC TCT
Val Leu Gly Glu Ala Gln Lys Leu Asn Asp Ser

CAA GCT CCA AAA GCT GAT GCG CAA CAA AAT AAG
Gln Ala Pro Lys Ala Asp Ala Gln Gln Asn Lys
        ←— E ——|—— D ——→

TTC AAC AAA GAT CAA CAA AGC GCC TTC TAT GAA
Phe Asn Lys Asp Gln Gln Ser Ala Phe Tyr Glu

ATC TTG AAC ATG CCT AAC TTA AAC GAG GAG CAA
Ile Leu Asn Met Pro Asn Leu Asn Glu Glu Gln

CGC AAT GGT TTC ATT CAA AGT CTT AAA GAC GAT
Arg Asn Gly Phe Ile Gln Ser Leu Lys Asp Asp

CCA AGC CAA AGC ACT AAC GTT TTA GGT GAA GCT
Pro Ser Gln Ser Thr Asn Val Leu Gly Glu Ala

AAA AAA TTA AAC GAA TCT CAA GCA CCG AAA GCT
Lys Lys Leu Asn Glu Ser Gln Ala Pro Lys Ala
                                ←— D ——|— A →

GAC AAC AAT TTC AAC AAA GAA CAA CAA AAT GCT
Asp Asn Asn Phe Asn Lys Glu Gln Gln Asn Ala

TTC TAT GAA ATC TTG AAC ATG CCT AAC TTG AAC
Phe Tyr Glu Ile Leu Asn Met Pro Asn Leu Asn

GAA GAA CAA CGC AAT GGT TTC ATC CAA AGC TTA
Glu Glu Gln Arg Asn Gly Phe Ile Gln Ser Leu

AAA GAT GAC CCA AGT CAA AGT GCT AAC CTT TTA
Lys Asp Asp Pro Ser Gln Ser Ala Asn Leu Leu

GCA GAA GCT AAA AAG TTA AAT GAA TCT CAA GCA
Ala Glu Ala Lys Lys Leu Asn Glu Ser Gln Ala

CCG AAA GCT GAT AAC AAA TTC AAC AAA GAA CAA
Pro Lys Ala Asp Asn Lys Phe Asn Lys Glu Gln
    ←— A ——|—— B ——→

CAA AAT GCT TTC TAT GAA ATC TTA CAT TTA CCT
Gln Asn Ala Phe Tyr Glu Ile Leu His Leu Pro

AAC TTA AAT GAA GAA CAA CGC AAT GGT TTC ATC
Asn Leu Asn Glu Glu Gln Arg Asn Gly Phe Ile

CAA AGC TTA AAA GAT GAC CCA AGC CAA AGC GCT
Gln Ser Leu Lys Asp Asp Pro Ser Gln Ser Ala

AAC CTT TTA GCA GAA GCT AAA AAG CTA AAT GAT
Asn Leu Leu Ala Glu Ala Lys Lys Leu Asn Asp

GCA CAA GCA CCA AAA GCT GAC AAC AAA TTC AAC
Ala Gln Ala Pro Lys Ala Asp Asn Lys Phe Asn
        ←— B ——|—— C ——→

AAA GAA CAA CAA AAT GCT TTC TAT GAA ATT TTA
Lys Glu Gln Gln Asn Ala Phe Tyr Glu Ile Leu

CAT TTA CCT AAC TTA ACT GAA GAA CAA CGT AAC
His Leu Pro Asn Leu Thr Glu Glu Gln Arg Asn

GGC TTC ATC CAA AGC CTT AAA GAC GAT CCT TCA
Gly Phe Ile Gln Ser Leu Lys Asp Asp Pro Ser
```

-continued

```
GTG AGC AAA GAA ATT TTA GCA GAA GCT AAA AAG
Val Ser Lys Glu Ile Leu Ala Glu Ala Lys Lys

CTA AAC GAT GCT CAA GCA CCA AAA GAG GAA GAC
Leu Asn Asp Ala Gln Ala Pro Lys Glu Glu Asp
        ←— C ——|

AAC AAC AAG CCT GGT AAA GAA GAC GGC AAC AAA
Asn Asn Lys Pro Gly Lys Glu Asp Gly Asn Lys

CCT GGT AAA GAA GAC GGC AAC AAA CCT GGT AAA
Pro Gly Lys Glu Asp Gly Asn Lys Pro Gly Lys

GAA GAC AAC AAA AAC CTT GGC AAA GAA GAC GGC
Glu Asp Asn Lys Asn Leu Gly Lys Glu Asp Gly

AAC AAA CCT GGT AAA GAA GAC AAC AAA AAA CCT
Asn Lys Pro Gly Lys Glu Asp Asn Lys Lys Pro

GGC AAA GAA GAT GGC AAC AAA CCT GGT AAA GAA
Gly Lys Glu Asp Gly Asn Lys Pro Gly Lys Glu

GAC GGC AAC AAG CCT GGT AAA GAA GAT GGC AAC
Asp Gly Asn Lys Pro Gly Lys Glu Asp Gly Asn

AAA CCT GGT AAA GAA GAT GGC AAC AAG CCT GGT
Lys Pro Gly Lys Glu Asp Gly Asn Lys Pro Gly

AAA GAA GAT GGC AAC AAG CCT CGT AAA GAA GAC
Lys Glu Asp Gly Asn Lys Pro Gly Lys Glu Asp

GGC AAC GGA GTA CAT GTC GTT AAA CCT GGT GAT
Gly Asn Gly Val His Val Val Lys Pro Gly Asp

ACA GTA AAT GAC ATT GCA AAA GCA AAC GGC ACT
Thr Val Asn Asp Ile Ala Lys Ala Asn Gly Thr

ACT GCT GAC AAA ATT GCT GCA GAT AAC AAA TTA
Thr Ala Asp Lys Ile Ala Ala Asp Asn Lys Leu

GCT GAT AAA AAC ATG ATC AAA CCT GGT CAA GAA
Ala Asp Lys Asn Met Ile Lys Pro Gly Gln Glu

CTT GTT GTT GAT AAG AAG CAA CCA GCA AAC CAT
Leu Val Val Asp Lys Lys Gln Pro Ala Asn His

GCA GAT GCT AAC AAA GCT CAA GCA TTA CCA GAA
Ala Asp Ala Asn Lys Ala Gln Ala Leu Pro Glu

ACT GGT GAA GAA AAT CCA TTC ATC GGT ACA ACT
Thr Gly Glu Glu Asn Pro Phe Ile Gly Thr Thr

GTA TTT GGT GGA TTA TCA TTA GCG TTA GGT GCA
Val Phe Gly Gly Leu Ser Leu Ala Leu Gly Ala

GCG TTA TTA GCT GGA CGT CGT CGC GAA CTA TAA
Ala Leu Leu Ala Gly Arg Arg Arg Glu Leu Stop.
```

2. A microorganism comprising a recombinant plasmid containing a nucleotide sequence coding for a fragment of the amino acid sequence of a protein A material, as defined in claim 1, said fragment having protein A biological activity.

3. A microorganism comprising a recombinant plasmid containing a nucleotide sequence coding for the amino acid sequence of a protein A material having a protein A biological activity, and equivalent nucleotide sequences coding for molecules with substantially the same protein A biological activity, said nucleotide sequence and said amino acid sequence are as follows:

TTG AAA AAG AAA AAC ATT TAT TCA ATT CGT AAA CTA GGT GTA GGT ATT GCA TCT GTA ACT TTA GGT
Met Lys Lys Lys Asn Ile Tyr Ser Ile Arg Lys Leu Gly Val Gly Ile Ala Ser Val Thr Leu Gly

-continued

```
ACA TTA CTT ATA TCT GGT GGC GTA ACA CCT GCT GCA AAT GCT GCG CAA CAC GAT GAA GCT CAA CAA
Thr Leu Leu Ile Ser Gly Gly Val Thr Pro Ala Ala Asn Ala Ala Gln His Asp Glu Ala Gln Gln
                                                                            |—— E ——>

AAT GCT TTT TAT CAA GTG TTA AAT ATG CCT AAC TTA AAC GCT GAT CAA CGT AAT GGT TTT ATC CAA
Asn Ala Phe Tyr Gln Val Leu Asn Met Pro Asn Leu Asn Ala Asp Gln Arg Asn Gly Phe Ile Gln

AGC CTT AAA GAT GAT CCA AGC CAA AGT GCT AAC GTT TTA GGT GAA GCT CAA AAA CTT AAT GAC TCT
Ser Leu Lys Asp Asp Pro Ser Gln Ser Ala Asn Val Leu Gly Glu Ala Gln Lys Leu Asn Asp Ser

CAA GCT CCA AAA GCT GAT GCG CAA CAA AAT AAG TTC AAC AAA GAT CAA CAA AGC GCC TTC TAT GAA
Gln Ala Pro Lys Ala Asp Ala Gln Gln Asn Lys Phe Asn Lys Asp Gln Gln Ser Ala Phe Tyr Glu
    <—— E ——|—— D ——>

ATC TTG AAC ATG CCT AAC TTA AAC GAG GAG CAA CGC AAT GGT TTC ATT CAA AGT CTT AAA GAC GAT
Ile Leu Asn Met Pro Asn Leu Asn Glu Glu Gln Arg Asn Gly Phe Ile Gln Ser Leu Lys Asp Asp

CCA AGC CAA AGC ACT AAC GTT TTA GGT GAA GCT AAA AAA TTA AAC GAA TCT CAA GCA CCG AAA GCT
Pro Ser Gln Ser Thr Asn Val Leu Gly Glu Ala Lys Lys Leu Asn Glu Ser Gln Ala Pro Lys Ala
                                                                     <—— D ——|—A—>

GAC AAC AAT TTC AAC AAA GAA CAA CAA AAT GCT TTC TAT GAA ATC TTG AAC ATG CCT AAC TTG AAC
Asp Asn Asn Phe Asn Lys Glu Gln Gln Asn Ala Phe Tyr Glu Ile Leu Asn Met Pro Asn Leu Asn

GAA GAA CAA CGC AAT GGT TTC ATC CAA AGC TTA AAA GAT GAC CCA AGT CAA AGT GCT AAC CTT TTA
Glu Glu Gln Arg Asn Gly Phe Ile Gln Ser Leu Lys Asp Asp Pro Ser Gln Ser Ala Asn Leu Leu

GCA GAA GCT AAA AAG TTA AAT GAA TCT CAA GCA CCG AAA GCT GAT AAC AAA TTC AAC AAA GAA CAA
Ala Glu Ala Lys Lys Leu Asn Glu Ser Gln Ala Pro Lys Ala Asp Asn Lys Phe Asn Lys Glu Gln
                                         <—— A ——|—— B ——>

CAA AAT GCT TTC TAT GAA ATC TTA CAT TTA CCT AAC TTA AAT GAA GAA CAA CGC AAT GGT TTC ATC
Gln Asn Ala Phe Tyr Glu Ile Leu His Leu Pro Asn Leu Asn Glu Glu Gln Arg Asn Gly Phe Ile

CAA AGC TTA AAA GAT GAC CCA AGC CAA AGC GCT AAC CTT TTA GCA GAA GCT AAA AAG CTA AAT GAT
Gln Ser Leu Lys Asp Asp Pro Ser Gln Ser Ala Asn Leu Leu Ala Glu Ala Lys Lys Leu Asn Asp

GCA CAA GCA CCA AAA GCT GAC AAC AAA TTC AAC AAA GAA CAA CAA AAT GCT TTC TAT GAA ATT TTA
Ala Gln Ala Pro Lys Ala Asp Asn Lys Phe Asn Lys Glu Gln Gln Asn Ala Phe Tyr Glu Ile Leu
    <—— B ——|—— C ——>

CAT TTA CCT AAC TTA ACT GAA GAA CAA CGT AAC GGC TTC ATC CAA AGC CTT AAA GAC GAT CCT TCA
His Leu Pro Asn Leu Thr Glu Glu Gln Arg Asn Gly Phe Ile Gln Ser Leu Lys Asp Asp Pro Ser.
```

4. A DNA transfer vector comprising a nucleotide sequence encoding an amino acid sequence as follows:

Met Lys Lys Lys Asn Ile Tyr Ser Ile Arg Lys Leu Gly Val Gly Ile Ala Ser Val Thr Leu Gly

Thr Leu Leu Ile Ser Gly Gly Val Thr Pro Ala Ala Asn Ala Ala Gln His Asp Glu Ala Gln Gln
|—E—>

Asn Ala Phe Tyr Gln Val Leu Asn Met Pro Asn Leu Asn Ala Asp Gln Arg Asn Gly Phe Ile Gln

Ser Leu Lys Asp Asp Pro Ser Gln Ser Ala Asn Val Leu Gly Glu Ala Gln Lys Leu Asn Asp Ser

Gln Ala Pro Lys Ala Asp Ala Gln Gln Asn Lys Phe Asn Lys Asp Gln Gln Ser Ala Phe Tyr Glu
<—E——|—D—>

Ile Leu Asn Met Pro Asn Leu Asn Glu Glu Gln Arg Asn Gly Phe Ile Gln Ser Leu Lys Asp Asp

Pro Ser Gln Ser Thr Asn Val Leu Gly Glu Ala Lys Lys Leu Asn Glu Ser Gln Ala Pro Lys Ala
<—D——|—A—

Asp Asn Asn Phe Asn Lys Glu Gln Gln Asn Ala Phe Tyr Glu Ile Leu Asn Met Pro Asn Leu Asn

Glu Glu Gln Arg Asn Gly Phe Ile Gln Ser Leu Lys Asp Asp Pro Ser Gln Ser Ala Asn Leu Leu

-continued

Ala Glu Ala Lys Lys Leu Asn Glu Ser Gln Ala Pro Lys Ala Asp Asn Lys Phe Asn Lys Glu Gln
⟵——A——|——B——⟶

Gln Asn Ala Phe Tyr Glu Ile Leu His Leu Pro Asn Leu Asn Glu Glu Gln Arg Asn Gly Phe Ile

Gln Ser Leu Lys Asp Asp Pro Ser Gln Ser Ala Asn Leu Leu Ala Glu Ala Lys Lys Leu Asn Asp

Ala Gln Ala Pro Lys Ala Asp Asn Lys Phe Asn Lys Glu Gln Gln Asn Ala Phe Tyr Glu Ile Leu
⟵——B——|——C——⟶

His Leu Pro Asn Leu Thr Glu Glu Gln Arg Asn Gly Phe Ile Gln Ser Leu Lys Asp Asp Pro Ser

Val Ser Lys Glu Ile Leu Ala Glu Ala Lys Lys Leu Asn Asp Ala Gln Ala Pro Lys Glu Glu Asp
⟵——C——|

Asn Asn Lys Pro Gly Lys Glu Asp Gly Asn Lys Pro Gly Lys Glu Asp Gly Asn Lys Pro Gly Lys

Glu Asp Asn Lys Asn Leu Gly Lys Glu Asp Gly Asn Lys Pro Gly Lys Glu Asn Asn Lys Lys Pro

Gly Lys Glu Asp Gly Asn Lys Pro Gly Lys Glu Asp Gly Asn Lys Pro Gly Lys Glu Asp Gly Asn

Lys Pro Gly Lys Glu Asp Gly Asn Lys Pro Gly Lys Glu Asp Gly Asn Lys Pro Gly Lys Glu Asp

Gly Asn Gly Val His Val Val Lys Pro Gly Asp Thr Val Asn Asp Ile Ala Lys Ala Asn Gly Thr

Thr Ala Asp Lys Ile Ala Ala Asp Asn Lys Leu Ala Asp Lys Asn Met Ile Lys Pro Gly Gln Glu

Leu Val Val Asp Lys Lys Gln Pro Ala Asn His Ala Asp Ala Asn Lys Ala Gln Ala Leu Pro Glu

Thr Gly Glu Glu Asn Pro Leu Ile Gly Thr Thr Val Phe Gly Gly Leu Ser Leu Ala Leu Gly Ala

Ala Leu Leu Ala Gly Arg Arg Arg Glu Leu.

5. The DNA transfer vector of claim 6 transferred to and replicated in a microorganism.

6. A DNA transfer vecvtor comprising a nucleotide sequence encoding an amino acid sequence as follows:

Met Lys Lys Lys Asn Ile Tyr Ser Ile Arg Lys Leu Gly Val Gly Ile Ala Ser Val Thr Leu Gly

Thr Leu Leu Ile Ser Gly Gly Val Thr Pro Ala Ala Asn Ala Ala Gln His Asp Glu Ala Gln Gln
|——E——⟶

Asn Ala Phe Tyr Gln Val Leu Asn Met Pro Asn Leu Asn Ala Asp Gln Arg Asn Gly Phe Ile Gln

Ser Leu Lys Asp Asp Pro Ser Gln Ser Ala Asn Val Leu Gly Glu Ala Gln Lye Leu Asn Asp Ser

Gln Ala Pro Lys Ala Asp Ala Gln Asn Lys Phe Asn Lys Asp Gln Gln Ser Ala Phe Tyr Glu
⟵——E——|——D——⟶

Ile Leu Asn Met Pro Asn Leu Asn Glu Glu Gln Arg Asn Gly Phe Ile Gln Ser Leu Lys Asp Asp

Pro Ser Gln Ser Thr Asn Val Leu Gly Glu Ala Lys Lys Leu Asn Glu Ser Gln Ala Pro Lys Ala
⟵——D——|——A——⟶

Asp Asn Asn Phe Asn Lys Glu Gln Gln Asn Ala Phe Tyr Glu Ile Leu Asn Met Pro Asn Leu Asn

Glu Glu Gln Arg Asn Gly Phe Ile Gln Ser Leu Lys Asp Asp Pro Ser Gln Ser Ala Asn Leu Leu

Ala Glu Ala Lys Lys Leu Asn Glu Ser Gln Ala Pro Lys Ala Asp Asn Lys Phe Asn Lys Glu Gln
⟵——A——|——B——⟶

Gln Asn Ala Phe Tyr Glu Ile Leu His Leu Pro Asn Leu Asp Glu Glu Gln Arg Asn Gly Phe Ile

Gln Ser Leu Lys Asp Asp Pro Ser Gln Ser Ala Asn Leu Leu Ala Glu Ala Lys Lys Leu Asp Asp

Ala Gln Ala Pro Lys Ala Asp Asn Lys Phe Asn Lys Glu Gln Gln Asn Ala Phe Tyr Glu Ile Leu
⟵——B——|——C——⟶

His Leu Pro Asn Leu Thr Glu Glu Gln Arg Asn Gly Phe Ile Gln Ser Leu Lys Asp Asp Pro Ser.

7. The DNA transfer vector of claim 6 transferred to and replicated in a microorganism.

8. Plasmid pAc37 comprising the entire genome of pBR322 and the nucleotide sequence defined in claim 4.

9. Plasmid pAc37-6 comprising the entire genome of pBR322 and the nucleotide sequence defined in claim 6.

10. *E. coli* deposit number NRRL B-15127, a microorganism according to claim 1.

11. *E. coli* deposit number NRRL B-15131, a microorganism according to claim 3.

12. A microorganism comprising a recombinant plasmid containing a nucleotide sequence coding for the amino acid sequence of domain D of a protein A material having domain D biological activity, and equivalent nucleotide sequences coding for molecules with substantially the same domain D biological activity, said nucleotide sequence and said amino acid sequence are as follows:

```
GCT GAT GCG CAA CAA AAT AAG TTC AAC AAA GAT CAA CAA AGC
Ala Asp Ala Gln Gln Asn Lys Phe Asn Lys Asp Gln Gln Ser

GCC TTC TAT GAA ATC TTG AAC ATG CCT AAC TTA AAC GAG GAG
Ala Phe Tyr Glu Ile Leu Asn Met Pro Asn Leu Asn Glu Glu

CAA CGC AAT GGT TTC ATT CAA AGT CTT AAA GAC GAT CCA AGC
Gln Arg Asn Gly Phe Ile Gln Ser Leu Lys Asp Asp Pro Ser

CAA AGC ACT AAC GTT TTA GGT GAA GCT AAA AAA TTA AAC GAA
Gln Ser Thr Asn Val Leu Gly Glu Ala Lys Lys Leu Asn Glu

TCT CAA GCA CCG AAA
Ser Gln Ala Pro Lys .
```

13. A microorganism comprising a recombinant plasmid containing a nucleotide sequence coding for the amino acid sequence of domain A of a protein A material having domain A biological activity and equivalent nucleotide sequences coding for molecules with substantially the same domain A biological activity, said nucleotide sequence and said amino acid sequence are as follows:

```
GCT GAC AAC AAT TTC AAC AAA GAA CAA CAA AAT GCT TTC TAT
Ala Asp Asn Asn Phe Asn Lys Glu Gln Gln Asn Ala Phe Tyr

GAA ATC TTG AAC ATG CCT AAC TTG AAC GAA GAA CAA CGC AAT
Glu Ile Leu Asn Met Pro Asn Leu Asn Glu Glu Gln Arg Asn

GGT TTC ATC CAA AGC TTA AAA GAT GAC CCA AGT CAA AGT GCT
Gly Phe Ile Gln Ser Leu Lys Asp Asp Pro Ser Gln Ser Ala

AAC CTT TTA GCA GAA GCT AAA AAG TTA AAT GAA TCT CAA GCA
Asn Leu Leu Ala Glu Ala Lys Lys Leu Asn Glu Ser Gln Ala

CCG AAA
Pro Lys .
```

14. A microorganism comprising a recombinant plasmid containing a nucleotide sequence coding for the amino acid sequence of domain B of a protein A material having domain B biological activity, and equivalent nucleotide sequences coding for molecules with substantially the same domain B biological activity, said nucleotide sequence and said amino acid sequence are as follows:

```
GCT GAT AAC AAA TTC AAC AAA GAA CAA CAA AAT GCT TTC TAT
Ala Asp Asn Lys Phe Asn Lys Glu Gln Gln Asn Ala Phe Tyr

GAA ATC TTA CAT TTA CCT AAC TTA AAT GAA GAA CAA CGC AAT
Glu Ile Leu His Leu Pro Asn Leu Asn Glu Glu Gln Arg Asn

GGT TTC ATC CAA AGC TTA AAA GAT GAC CCA AGC CAA AGC GCT
Gly Phe Ile Gln Ser Leu Lys Asp Asp Pro Ser Gln Ser Ala

AAC CTT TTA GCA GAA GCT AAA AAG CTA AAT GAT GCA CAA GCA
Asn Leu Leu Ala Glu Ala Lys Lys Leu Asn Asp Ala Gln Ala

CCA AAA
Pro Lys .
```

15. A microorganism comprising a recombinant plasmid containing a nucleotide sequence coding for the amino acid sequence of domain C of a protein A material having domain C biological activity and equivalent nucleotide sequences coding for molecules with substantially the same domain C biological activity, said nucleotide sequence and said amino acid sequence are as follows:

```
GCT GAC AAC AAA TTC AAC AAA GAA CAA CAA AAT GCT TTC TAT
Ala Asp Asn Lys Phe Asn Lys Glu Gln Gln Asn Ala Phe Tyr

GAA ATT TTA CAT TTA CCT AAC TTA ACT GAA GAA CAA CGT AAC
Glu Ile Leu His Leu Pro Asn Leu Thr Glu Glu Gln Arg Asn
```

```
GGC TTC ATC CAA AGC CTT AAA GAC GAT CCT TCA GTG AGC AAA
Gly Phe Ile Gln Ser Leu Lys Asp Asp Pro Ser Val Ser Lys

GAA ATT TTA GCA GAA GCT AAA AAG CTA AAC GAT GCT CAA GCA
Glu Ile Leu Ala Glu Ala Lys Lys Leu Asn Asp Ala Gln Ala

CCA AAA
Pro Lys .
```

16. A microorganism comprising a recombinant plasmid containing a nucleotide sequence coding for the amino acid sequence of domain E of a protein A material having domain E biological activity, and equivalent nucleotide sequences coding for molecules with substantially the same domain E biological activity, said nucleotide sequence and said amino acid sequence are as follows:

```
GCT CAA CAA AAT GCT TTT TAT CAA GTG TTA AAT ATG CCT AAC
Ala Gln Gln Asn Ala Phe Tyr Gln Val Leu Asn Met Pro Asn

TTA AAC GCT GAT CAA CGT AAT GGT TTT ATC CAA AGC CTT AAA
Leu Asn Ala Asp Gln Arg Asn Gly Phe Ile Gln Ser Leu Lys

GAT GAT CCA AGC CAA AGT GCT AAC GTT TTA GGT GAA GCT CAA
Asp Asp Pro Ser Gln Ser Ala Asn Val Leu Gly Glu Ala Gln

AAA CTT AAT GAC TCT CAA GCT CCA AAA
Lys Leu Asn Asp Ser Gln Ala Pro Lys .
```

17. A microorganism comprising a recombinant plasmid containing a nucleotide sequence coding for the amino acid sequence of the carboxy terminal domain of a protein A material having a protein A biological activity, and equivalent nucleotide sequences coding for molecules with substantially the same biological activity, said nucleotide sequence and said amino acid sequence are as follows:

```
GAG GAA GAC AAC AAC AAG CCT GGT AAA GAA GAC GGC AAC AAA
Glu Glu Asp Asn Asn Lys Pro Gly Lys Glu Asp Gly Asn Lys

CCT GGT AAA GAA GAC GGC AAC AAA CCT GGT AAA GAA GAC AAC
Pro Gly Lys Glu Asp Gly Asn Lys Pro Gly Lys Glu Asp Asn

AAA AAC CTT GGC AAA GAA GAC GGC AAC AAA CCT GGT AAA GAA
Lys Asn Leu Gly Lys Glu Asp Gly Asn Lys Pro Gly Lys Glu

GAC AAC AAA AAA CCT GGC AAA GAA GAT GGC AAC AAA CCT GGT
Asp Asn Lys Lys Pro Gly Lys Glu Asp Gly Asn Lys Pro Gly

AAA GAA GAC GGC AAC AAG CCT GGT AAA GAA GAT GGC AAC AAA
Lys Glu Asp Gly Asn Lys Pro Gly Lys Glu Asp Gly Asn Lys

CCT GGT AAA GAA GAT GGC AAC AAG CCT GGT AAA GAA GAT GGC
Pro Gly Lys Glu Asp Gly Asn Lys Pro Gly Lys Glu Asp Gly

AAC AAG CCT GGT AAA GAA GAC GGC AAC GGA GTA CAT GTC GTT
Asn Lys Pro Gly Lys Glu Asp Gly Asn Gly Val His Val Val

AAA CCT GGT GAT ACA GTA AAT GAC ATT GCA AAA GCA AAC GGC
Lys Pro Gly Asp Thr Val Asn Asp Ile Ala Lys Ala Asn Gly

ACT ACT GCT GAC AAA ATT GCT GCA GAT AAC AAA TTA GCT GAT
Thr Thr Ala Asp Lys Ile Ala Ala Asp Asn Lys Leu Ala Asp

AAA AAC ATG ATC AAA CCT GGT CAA GAA CTT GTT GTT GAT AAG
Lys Asn Met Ile Lys Pro Gly Gln Glu Leu Val Val Asp Lys

AAG CAA CCA GCA AAC CAT GCA GAT GCT AAC AAA GCT CAA GCA
Lys Gln Pro Ala Asn His Ala Asp Ala Asn Lys Ala Gln Ala

TTA CCA GAA ACT GGT GAA GAA AAT CCA TTC ATC GGT ACA ACT
Leu Pro Glu Thr Gly Glu Glu Asn Pro Leu Ile Gly Thr Thr

GTA TTT GGT GGA TTA TCA TTA GCG TTA GGT GCA GCG TTA TTA
Val Phe Gly Gly Leu Ser Leu Ala Leu Gly Ala Ala Leu Leu

GCT GGA CGT CGT CGC GAA CTA TAA
Ala Gly Arg Arg Arg Glu Leu Stop .
```

18. A microorganism comprising a recombinant plasmid containing a mixture of nucleotide sequences of domains E, D, A, B, and C coding for amino acid sequences having a protein A biological activity, and equivalent nucleotide sequences coding for substantially the same biological activity.

19. An essentially pure nucleotide sequence coding for the amino acid sequence of a protein A material having a protein A biological activity, said nucleotide sequence and amino acid sequence are as follows:

```
TTG AAA AAG AAA AAC ATT TAT TCA ATT CGT AAA CTA GGT GTA GGT ATT GCA TCT GTA ACT TTA GGT
Met Lys Lys Lys Asn Ile Tyr Ser Ile Arg Lys Leu Gly Val Gly Ile Ala Ser Val Thr Leu Gly

ACA TTA CTT ATA TCT GGT GGC GTA ACA CCT GCT GCA AAT GCT GCG CAA CAC GAT GAA GCT CAA CAA
Thr Leu Leu Ile Ser Gly Gly Val Thr Pro Ala Ala Asn Ala Ala Gln His Asp Glu Ala Gln Gln
                                                                        |——E——>

AAT GCT TTT TAT CAA GTG TTA AAT ATG CCT AAC TTA AAC GCT GAT CAA CGT AAT GGT TTT ATC CAA
Asn Ala Phe Tyr Gln Val Leu Asn Met Pro Asn Leu Asn Ala Asp Gln Arg Asn Gly Phe Ile Gln

AGC CTT AAA GAT GAT CCA AGC CAA AGT GCT AAC GTT TTA GGT GAA GCT CAA AAA CTT AAT GAC TCT
Ser Leu Lys Asp Asp Pro Ser Gln Ser Ala Asn Val Leu Gly Glu Ala Gln Lys Leu Asn Asp Ser

CAA GCT CCA AAA GCT GAT GCG CAA CAA AAT AAG TTC AAC AAA GAT CAA CAA AGC GCC TTC TAT GAA
Gln Ala Pro Lys Ala Asp Ala Gln Gln Asn Lys Phe Asn Lys Asp Gln Gln Ser Ala Phe Tyr Glu
       <——E——|——D——>

ATC TTG AAC ATG CCT AAC TTA AAC GAG GAG CAA CGC AAT GGT TTC ATT CAA AGT CTT AAA GAC GAT
Ile Leu Asn Met Pro Asn Leu Asn Glu Glu Gln Arg Asn Gly Phe Ile Gln Ser Leu Lys Asp Asp

CCA AGC CAA AGC ACT AAC GTT TTA GGT GAA GCT AAA AAA TTA AAC GAA TCT CAA GCA CCG AAA GCT
Pro Ser Gln Ser Thr Asn Val Leu Gly Glu Ala Lys Lys Leu Asn Glu Ser Gln Ala Pro Lys Ala
                                                                  <——D——|——A——>

GAC AAC AAT TTC AAC AAA GAA CAA CAA AAT GCT TTC TAT GAA ATC TTC AAC ATG CCT AAC TTC AAC
Asp Asn Asn Phe Asn Lys Glu Gln Gln Asn Ala Phe Tyr Glu Ile Leu Asn Met Pro Asn Leu Asn

GAA GAA CAA CGC AAT GGT TTC ATC CAA AGC TTA AAA GAT GAC CCA AGT CAA AGT GCT AAC CTT TTA
Glu Glu Gln Arg Asn Gly Phe Ile Gln Ser Leu Lys Asp Asp Pro Ser Gln Ser Ala Asn Leu Leu

GCA GAA GCT AAA AAG TTA AAT GAA TCT CAA GCA CCG AAA GCT GAT AAC AAA TTC AAC AAA GAA CAA
Ala Glu Ala Lys Lys Leu Asn Glu Ser Gln Ala Pro Lys Ala Asp Asn Lys Phe Asn Lys Glu Gln
                                        <——A——|——B——>

CAA AAT GCT TTC TAT GAA ATC TTA CAT TTA CCT AAC TTA AAT GAA GAA CAA CGC AAT GGT TTC ATC
Gln Asn Ala Phe Tyr Glu Ile Leu His Leu Pro Asn Leu Asn Glu Glu Gln Arg Asn Gly Phe Ile

CAA AGC TTA AAA GAT GAC CCA AGC CAA AGC GCT AAC CTT TTA GCA GAA GCT AAA AAC CTA AAT GAT
Gln Ser Leu Lys Asp Asp Pro Ser Gln Ser Ala Asn Leu Leu Ala Glu Ala Lys Lys Leu Asn Asp

GCA CAA GCA CCA AAA GCT GAC AAC AAA TTC AAC AAA GAA CAA CAA AAT GCT TTC TAT GAA ATT TTA
Ala Gln Ala Pro Lys Ala Asp Asn Lys Phe Asn Lys Glu Gln Gln Asn Ala Phe Tyr Glu Ile Leu
       <——B——|——C——>

CAT TTA CCT AAC TTA ACT GAA GAA CAA CGT AAC GGC TTC ATC CAA AGC CTT AAA GAC GAT CCT TCA
His Leu Pro Asn Leu Thr Glu Glu Gln Arg Asn Gly Phe Ile Gln Ser Leu Lys Asp Asp Pro Ser

GTG AGC AAA GAA ATT TTA GCA GAA GCT AAA AAG CTA AAC GAT GCT CAA GCA CCA AAA GAG GAA GAC
Val Ser Lys Glu Ile Leu Ala Glu Ala Lys Lys Leu Asn Asp Ala Gln Ala Pro Lys Glu Glu Asp
                                                                  <——C——|

AAC AAC AAG CCT GGT AAA GAA GAC GGC AAC AAA CCT GGT AAA GAA GAC GGC AAC AAA CCT GGT AAA
Asn Asn Lys Pro Gly Lys Glu Asp Gly Asn Lys Pro Gly Lys Glu Asp Gly Asn Lys Pro Gly Lys

GAA GAC AAC AAA AAC CTT GGC AAA GAA GAC GGC AAC AAA CCT GGT AAA GAA GAC AAC AAA AAA CCT
Glu Asp Asn Lys Asn Leu Gly Lys Glu Asp Gly Asn Lys Pro Gly Lys Glu Asp Asn Lys Lys Pro

GGC AAA GAA GAT GGC AAC AAA CCT GGT AAA GAA GAC GGC AAC AAG CCT GGT AAA GAA GAT GGC AAC
Gly Lys Glu Asp Gly Asn Lys Pro Gly Lys Glu Asp Gly Asn Lys Pro Gly Lys Glu Asp Gly Asn

AAA CCT GCT AAA GAA GAT GGC AAC AAG CCT GGT AAA GAA GAT GGC AAC AAG CCT CGT AAA GAA GAC
Lys Pro Gly Lys Glu Asp Gly Asn Lys Pro Gly Lys Glu Asp Gly Asn Lys Pro Gly Lys Glu Asp

GGC AAC GGA GTA CAT GTC GTT AAA CCT GCT GAT ACA GTA AAT GAC ATT GCA AAA GCA AAC GGC ACT
Gly Asn Gly Val His Val Val Lys Pro Gly Asp Thr Val Asn Asp Ile Ala Lys Ala Asn Gly Thr

ACT GCT GAC AAA ATT GCT GCA GAT AAC AAA TTA GCT GAT AAA AAC ATG ATC AAA CCT GGT CAA GAA
Thr Ala Asp Lys Ile Ala Ala Asp Asn Lys Leu Ala Asp Lys Asn Met Ile Lys Pro Gly Gln Glu
```

-continued

```
CTT GTT GTT GAT AAG AAG CAA CCA GCA AAC CAT CGA GAT GCT AAC AAA GCT CAA GCA TTA CCA GAA
Leu Val Val Asp Lys Lys Gln Pro Ala Asn His Ala Asp Ala Asn Lys Ala Gln Ala Leu Pro Glu

ACT GGT GAA GAA AAT CCA TTC ATC GGT ACA ACT GTA TTT GGT GGA TTA TCA TTA GCG TTA GGT GCA
Thr Gly Glu Glu Asn Pro Leu Ile Gly Thr Thr Val Phe Gly Gly Leu Ser Leu Ala Leu Gly Ala

GCG TTA TTA GCT GGA CGT CGT CGC GAA CTA TAA
Ala Leu Leu Ala Gly Arg Arg Arg Glu Leu Stop.
```

20. An essentially pure nucleotide sequence coding for the amino acid sequence of domain E of a protein A material having domain E biological activity, and equivalent nucleotide sequences coding for molecules with substantially the same domain E biological activity, said nucleotide sequence and said amino acid sequence are as follows:

```
GCT CAA CAA AAT GCT TTT TAT CAA GTG TTA AAT ATG CCT AAC
Ala Gln Gln Asn Ala Phe Tyr Gln Val Leu Asn Met Pro Asn

TTA AAC GCT GAT CAA CGT AAT GGT TTT ATC CAA AGC CTT AAA
Leu Asn Ala Asp Gln Arg Asn Gly Phe Ile Gln Ser Leu Lys

GAT GAT CCA AGC CAA AGT GCT AAC GTT TTA GGT GAA GCT CAA
Asp Asp Pro Ser Gln Ser Ala Asn Val Leu Gly Glu Ala Gln

AAA CTT AAT GAC TCT CAA GCT CCA AAA
Lys Leu Asn Asp Ser Gln Ala Pro Lys.
```

21. A process for producing a protein A material having a protein A biological activity which comprises expression of cloned DNA, said cloned DNA comprising a nucleotide sequence coding for the amino acid sequence of said protein A material, and equivalent nucleotide sequences coding for molecules with substantially the same protein A biological activity, in a suitable microbial host, and recovering said protein A material; said nucleotide sequence and amino acid sequence are as follows:

```
TTG AAA AAG AAA AAC ATT TAT TCA ATT CGT AAA CTA GGT GTA GGT ATT GCA TCT GTA ACT TTA GGT
Met Lys Lys Lys Asn Ile Tyr Ser Ile Arg Lys Leu Gly Val Gly Ile Ala Ser Val Thr Leu Gly

ACA TTA CTT ATA TCT GGT GGC GTA ACA CCT GCT GCA AAT GCT GCG CAA CAC GAT GAA GCT CAA CAA
Thr Leu Leu Ile Ser Gly Gly Val Thr Pro Ala Ala Asn Ala Ala Gln His Asp Glu Ala Gln Gln
                                                                      |——E——>

AAT GCT TTT TAT CAA GTG TTA AAT ATG CCT AAC TTA AAC GCT GAT CAA CGT AAT GGT TTT ATC CAA
Asn Ala Phe Tyr Gln Val Leu Asn Met Pro Asn Leu Asn Ala Asp Gln Arg Asn Gly Phe Ile Gln

AGC CTT AAA GAT GAT CCA AGC CAA AGT GCT AAC GTT TTA GGT GAA GCT CAA AAA CTT AAT GAC TCT
Ser Leu Lys Asp Asp Pro Ser Gln Ser Ala Asn Val Leu Gly Glu Ala Gln Lys Leu Asn Asp Ser

CAA GCT CCA AAA GCT GAT GCG CAA CAA AAT AAG TTC AAC AAA GAT CAA CAA AGC GCC TTC TAT GAA
Gln Ala Pro Lys Ala Asp Ala Gln Gln Asn Lys Phe Asn Lys Asp Gln Gln Ser Ala Phe Tyr Glu
<——E——|——D——>

ATC TTG AAC ATG CCT AAC TTA AAC GAG GAG CAA CGC AAT GGT TTC ATT CAA AGT CTT AAA GAC GAT
Ile Leu Asn Met Pro Asn Leu Asn Glu Glu Gln Arg Asn Gly Phe Ile Gln Ser Leu Lys Asp Asp

CCA AGC CAA AGC ACT AAC GTT TTA GGT GAA GCT AAA AAA TTA AAC GAA TCT CAA GCA CCG AAA GCT
Pro Ser Gln Ser Thr Asn Val Leu Gly Glu Ala Lys Lys Leu Asn Glu Ser Gln Ala Pro Lys Ala
                                                                      <——D——|——A——>

GAC AAC AAT TTC AAC AAA GAA CAA CAA AAT GCT TTC TAT GAA ATC TTC AAC ATG CCT AAC TTC AAC
Asp Asn Asn Phe Asn Lys Glu Gln Gln Asn Ala Phe Tyr Glu Ile Leu Asn Met Pro Asn Leu Asn

GAA GAA CAA CGC AAT GGT TTC ATC CAA AGC TTA AAA GAT GAC CCA AGT CAA AGT GCT AAC CTT TTA
Glu Glu Gln Arg Asn Gly Phe Ile Gln Ser Leu Lys Asp Asp Pro Ser Gln Ser Ala Asn Leu Leu

GCA GAA GCT AAA AAG TTA AAT GAA TCT CAA GCA CCG AAA GCT GAT AAC AAA TTC AAC AAA GAA CAA
Ala Glu Ala Lys Lys Leu Asn Glu Ser Gln Ala Pro Lys Ala Asp Asn Lys Phe Asn Lys Glu Gln
                                                      <——A——|——B——>

CAA AAT GCT TTC TAT GAA ATC TTA CAT TTA CCT AAC TTA AAT GAA GAA CAA CGC AAT GGT TTC ATC
Gln Asn Ala Phe Tyr Glu Ile Leu His Leu Pro Asn Leu Asn Glu Glu Gln Arg Asn Gly Phe Ile

CAA AGC TTA AAA GAT GAC CCA AGC CAA AGC GCT AAC CTT TTA GCA GAA GCT AAA AAC CTA AAT GAT
Gln Ser Leu Lys Asp Asp Pro Ser Gln Ser Ala Asn Leu Leu Ala Glu Ala Lys Lys Leu Asn Asp
```

-continued

```
GCA CAA GCA CCA AAA GCT GAC AAC AAA TTC AAC AAA GAA CAA CAA AAT GCT TTC TAT GAA ATT TTA
Ala Gln Ala Pro Lys Ala Asp Asn Lys Phe Asn Lys Glu Gln Gln Asn Ala Phe Tyr Glu Ile Leu
         <—— B ——|—— C ——>

CAT TTA CCT AAC TTA ACT GAA GAA CAA CGT AAC GGC TTC ATC CAA AGC CTT AAA GAC GAT CCT TCA
His Leu Pro Asn Leu Thr Glu Glu Gln Arg Asn Gly Phe Ile Gln Ser Leu Lys Asp Asp Pro Ser

GTG AGC AAA GAA ATT TTA GCA GAA GCT AAA AAG CTA AAC GAT GCT CAA GCA CCA AAA GAG GAA GAC
Val Ser Lys Glu Ile Leu Ala Glu Ala Lys Lys Leu Asn Asp Ala Gln Ala Pro Lys Glu Glu Asp
                                                                <—— C ——|

AAC AAC AAG CCT GGT AAA GAA GAC GGC AAC AAA CCT GGT AAA GAA GAC GGC AAC AAA CCT GGT AAA
Asn Asn Lys Pro Gly Lys Glu Asp Gly Asn Lys Pro Gly Lys Glu Asp Gly Asn Lys Pro Gly Lys

GAA GAC AAC AAA AAC CTT GGC AAA GAA GAC GGC AAC AAA CCT GGT AAA GAA GAC AAC AAA AAA CCT
Glu Asp Asn Lys Asn Leu Gly Lys Glu Asp Gly Asn Lys Pro Gly Lys Glu Asp Asn Lys Lys Pro

GGC AAA GAA GAT GGC AAC AAA CCT GGT AAA GAA GAC GGC AAC AAG CCT GGT AAA GAA GAT GGC AAC
Gly Lys Glu Asp Gly Asn Lys Pro Gly Lys Glu Asp Gly Asn Lys Pro Gly Lys Glu Asp Gly Asn

AAA CCT GCT AAA GAA GAT GGC AAC AAG CCT GGT AAA GAA GAT GGC AAC AAG CCT CGT AAA GAA GAC
Lys Pro Gly Lys Glu Asp Gly Asn Lys Pro Gly Lys Glu Asp Gly Asn Lys Pro Gly Lys Glu Asp

GGC AAC GGA GTA CAT GTC GTT AAA CCT GCT GAT ACA GTA AAT GAC ATT GCA AAA GCA AAC GGC ACT
Gly Asn Gly Val His Val Val Lys Pro Gly Asp Thr Val Asn Asp Ile Ala Lys Ala Asn Gly Thr

ACT GCT GAC AAA ATT GCT GCA GAT AAC AAA TTA GCT GAT AAA AAC ATG ATC AAA CCT GGT CAA GAA
Thr Ala Asp Lys Ile Ala Ala Asp Asn Lys Leu Ala Asp Lys Asn Met Ile Lys Pro Gly Gln Glu

CTT GTT GTT GAT AAG AAG CAA CCA GCA AAC CAT CGA GAT GCT AAC AAA GCT CAA GCA TTA CCA GAA
Leu Val Val Asp Lys Lys Gln Pro Ala Asn His Ala Asp Ala Asn Lys Ala Gln Ala Leu Pro Glu

ACT GGT GAA GAA AAT CCA TTC ATC GGT ACA ACT GTA TTT GGT GGA TTA TCA TTA GCG TTA GGT GCA
Thr Gly Glu Glu Asn Pro Leu Ile Gly Thr Thr Val Phe Gly Gly Leu Ser Leu Ala Leu Gly Ala

GCG TTA TTA GCT GGA CGT CGT CGC GAA CTA TAA
Ala Leu Leu Ala Gly Arg Arg Arg Glu Leu Stop.
```

22. A process for preparing a protein A material having a protein A biological activity which comprises expression of cloned DNA, said cloned DNA comprising a nucleotide sequence coding for the amino acid sequence of said protein A material, and equivalent nucleotide sequences coding for molecules with substantially the same protein A biological activity, in a suitable microbial host, and recovering said protein A material; said nucleotide sequence and amino acid sequence are as follows:

```
TTG AAA AAG AAA AAC ATT TAT TCA ATT CGT AAA CTA GGT GTA GGT ATT GCA TCT GTA ACT TTA GGT
Met Lys Lys Lys Asn Ile Tyr Ser Ile Arg Lys Leu Gly Val Gly Ile Ala Ser Val Thr Leu Gly

ACA TTA CTT ATA TCT GGT GGC GTA ACA CCT GCT GCA AAT GCT GCG CAA CAC GAT GAA GCT CAA CAA
Thr Leu Leu Ile Ser Gly Gly Val Thr Pro Ala Ala Asn Ala Ala Gln His Asp Glu Ala Gln Gln
                                                                        |—— E ——>

AAT GCT TTT TAT CAA GTG TTA AAT ATG CCT AAC TTA AAC GCT GAT CAA CGT AAT GGT TTT ATC CAA
Asn Ala Phe Tyr Gln Val Leu Asn Met Pro Asn Leu Asn Ala Asp Gln Arg Asn Gly Phe Ile Gln

AGC CTT AAA GAT GAT CCA AGC CAA AGT GCT AAC GTT TTA GGT GAA GCT CAA AAA CTT AAT GAC TCT
Ser Leu Lys Asp Asp Pro Ser Gln Ser Ala Asn Val Leu Gly Glu Ala Gln Lys Leu Asn Asp Ser

CAA GCT CCA AAA GCT GAT GCG CAA CAA AAT AAG TTC AAC AAA GAT CAA CAA AGC GCC TTC TAT GAA
Gln Ala Pro Lys Ala Asp Ala Gln Gln Asn Lys Phe Asn Lys Asp Gln Gln Ser Ala Phe Tyr Glu
         <—— E ——|—— D ——>

ATC TTG AAC ATG CCT AAC TTA AAC GAG GAG CAA CGC AAT GGT TTC ATT CAA AGT CTT AAA GAC GAT
Ile Leu Asn Met Pro Asn Leu Asn Glu Glu Gln Arg Asn Gly Phe Ile Gln Ser Leu Lys Asp Asp

CCA AGC CAA AGC ACT AAC GTT TTA GGT GAA GCT AAA AAA TTA AAC GAA TCT CAA GCA CCG AAA GCT
Pro Ser Gln Ser Thr Asn Val Leu Gly Glu Ala Lys Lys Leu Asn Glu Ser Gln Ala Pro Lys Ala
                                                                <—— D ——|—— A ——>

GAC AAC AAT TTC AAC AAA GAA CAA CAA AAT GCT TTC TAT GAA ATC TTC AAC ATG CCT AAC TTC AAC
Asp Asn Asn Phe Asn Lys Glu Gln Gln Asn Ala Phe Tyr Glu Ile Leu Asn Met Pro Asn Leu Asn

GAA GAA CAA CGC AAT GGT TTC ATC CAA AGC TTA AAA GAT GAC CCA AGT CAA AGT GCT AAC CTT TTA
Glu Glu Gln Arg Asn Gly Phe Ile Gln Ser Leu Lys Asp Asp Pro Ser Gln Ser Ala Asn Leu Leu
```

-continued

```
GCA GAA GCT AAA AAG TTA AAT GAA TCT CAA GCA CCG AAA GCT GAT AAC AAA TTC AAC AAA GAA CAA
Ala Glu Ala Lys Lys Leu Asn Glu Ser Gln Ala Pro Lys Ala Asp Asn Lys Phe Asn Lys Glu Gln
                                        ←——A——|——B——→

CAA AAT GCT TTC TAT GAA ATC TTA CAT TTA CCT AAC TTA AAT GAA GAA CAA CGC AAT GGT TTC ATC
Gln Asn Ala Phe Tyr Glu Ile Leu His Leu Pro Asn Leu Asn Glu Glu Gln Arg Asn Gly Phe Ile

CAA AGC TTA AAA GAT GAC CCA AGC CAA AGC GCT AAC CTT TTA GCA GAA GCT AAA AAC CTA AAT GAT
Gln Ser Leu Lys Asp Asp Pro Ser Gln Ser Ala Asn Leu Leu Ala Glu Ala Lys Lys Leu Asn Asp

GCA CAA GCA CCA AAA GCT GAC AAC AAA TTC AAC AAA GAA CAA CAA AAT GCT TTC TAT GAA ATT TTA
Ala Gln Ala Pro Lys Ala Asp Asn Lys Phe Asn Lys Glu Gln Gln Asn Ala Phe Tyr Glu Ile Leu
            ←——B——|——C——→

CAT TTA CCT AAC TTA ACT GAA GAA CAA CGT AAC GGC TTC ATC CAA AGC CTT AAA GAC GAT CCT TCA
His Leu Pro Asn Leu Thr Glu Glu Gln Arg Asn Gly Phe Ile Gln Ser Leu Lys Asp Asp Pro Ser .
```

23. A process for preparing a protein A material having domain D biological activity which comprises expression of cloned DNA, said cloned DNA comprising a nucleotide sequence coding for the amino acid sequence of domain D of said protein A material, and equivalent nucleotide sequences coding for molecules with substantially the same domain A biological activity, in a suitable microbial host, and recovering said protein A material; said nucleotide sequence and amino acid sequence are as follows:

| GCT | GAC | AAC | AAT | TTC | AAC | AAA | GAA | CAA | CAA | AAT | GCT | TTC | TAT |
|-----|-----|-----|-----|-----|-----|-----|-----|-----|-----|-----|-----|-----|-----|
| Ala | Asp | Asn | Asn | Phe | Asn | Lys | Glu | Gln | Gln | Asn | Ala | Phe | Tyr |
| GAA | ATC | TTG | AAC | ATG | CCT | AAC | TTG | AAC | GAA | GAA | CAA | CGC | AAT |
| Glu | Ile | Leu | Asn | Met | Pro | Asn | Leu | Asn | Glu | Glu | Gln | Arg | Asn |
| GGT | TTC | ATC | CAA | AGC | TTA | AAA | GAT | GAC | CCA | AGT | CAA | AGT | GCT |
| Gly | Phe | Ile | Gln | Ser | Leu | Lys | Asp | Asp | Pro | Ser | Gln | Ser | Ala |
| AAC | CTT | TTA | GCA | GAA | GCT | AAA | AAG | TTA | AAT | GAA | TCT | CAA | GCA |
| Asn | Leu | Leu | Ala | Glu | Ala | Lys | Lys | Leu | Asn | Glu | Ser | Gln | Ala |
| CCG | AAA |     |     |     |     |     |     |     |     |     |     |     |     |
| Pro | Lys . |   |     |     |     |     |     |     |     |     |     |     |     | equivalent nucleotide sequences coding for molecules with substantially the same domain D biological activity, in a suitable microbial host, and recovering said protein A material; said nucleotide sequence and amino acid sequence are as follows:

25. A process for preparing protein A material having domain B biological activity which comprises expression of cloned DNA, said cloned DNA comprising a nucleotide sequence coding for the amino acid sequence of domain B of said protein A material, and equivalent

| GCT | GAT | GCG | CAA | CAA | AAT | AAG | TTC | AAC | AAA | GAT | CAA | CAA | AGC |
|-----|-----|-----|-----|-----|-----|-----|-----|-----|-----|-----|-----|-----|-----|
| Ala | Asp | Ala | Gln | Gln | Asn | Lys | Phe | Asn | Lys | Asp | Gln | Gln | Ser |
| GCC | TTC | TAT | GAA | ATC | TTG | AAC | ATG | CCT | AAC | TTA | AAC | GAG | GAG |
| Ala | Phe | Tyr | Glu | Ile | Leu | Asn | Met | Pro | Asn | Leu | Asn | Glu | Glu |
| CAA | CGC | AAT | GGT | TTC | ATT | CAA | AGT | CTT | AAA | GAC | GAT | CCA | AGC |
| Gln | Arg | Asn | Gly | Phe | Ile | Gln | Ser | Leu | Lys | Asp | Asp | Pro | Ser |
| CAA | AGC | ACT | AAC | GTT | TTA | GGT | GAA | GCT | AAA | AAA | TTA | AAC | GAA |
| Gln | Ser | Thr | Asn | Val | Leu | Gly | Glu | Ala | Lys | Lys | Leu | Asn | Glu |
| TCT | CAA | GCA | CCG | AAA |     |     |     |     |     |     |     |     |     |
| Ser | Gln | Ala | Pro | Lys . |   |     |     |     |     |     |     |     |     |

24. A process for preparing a protein A material having domain A biological activity which comprises expression of cloned DNA, said cloned DNA comprising a nucleotide sequence coding for the amino acid sequence of domain A of said protein A material, and nucleotide sequences coding for molecules with substantially the same domain B biological activity, in a suitable microbial host, and recovering said protein A material; said nucleotide sequence and amino acid sequence are as follows:

| GCT | GAT | AAC | AAA | TTC | AAC | AAA | GAA | CAA | CAA | AAT | GCT | TTC | TAT |
|-----|-----|-----|-----|-----|-----|-----|-----|-----|-----|-----|-----|-----|-----|
| Ala | Asp | Asn | Lys | Phe | Asn | Lys | Glu | Gln | Gln | Asn | Ala | Phe | Tyr |
| GAA | ATC | TTA | CAT | TTA | CCT | AAC | TTA | AAT | GAA | GAA | CAA | CGC | AAT |
| Glu | Ile | Leu | His | Leu | Pro | Asn | Leu | Asn | Glu | Glu | Gln | Arg | Asn |

-continued

| GGT | TTC | ATC | CAA | AGC | TTA | AAA | GAT | GAC | CCA | AGC | CAA | AGC | GCT |
|-----|-----|-----|-----|-----|-----|-----|-----|-----|-----|-----|-----|-----|-----|
| Gly | Phe | Ile | Gln | Ser | Leu | Lys | Asp | Asp | Pro | Ser | Gln | Ser | Ala |
| AAC | CTT | TTA | GCA | GAA | GCT | AAA | AAG | CTA | AAT | GAT | GCA | CAA | GCA |
| Asn | Leu | Leu | Ala | Glu | Ala | Lys | Lys | Leu | Asn | Asp | Ala | Gln | Ala |
| CCA | AAA |     |     |     |     |     |     |     |     |     |     |     |     |
| Pro | Lys . |   |     |     |     |     |     |     |     |     |     |     |     |

26. A process for preparing a protein A material having domain C biological activity which comprises expression of cloned DNA, said cloned DNA comprising a nucleotide sequence coding for the amino acid sequence of domain C of said protein A material, and equivalent nucleotide sequences coding for molecules with substantially the same domain C biological activity, in a suitable microbial host, and recovering said protein A material; said nucleotide sequence and amino acid sequence are as follows:

| GCT | GAC | AAC | AAA | TTC | AAC | AAA | GAA | CAA | CAA | AAT | GCT | TTC | TAT |
|-----|-----|-----|-----|-----|-----|-----|-----|-----|-----|-----|-----|-----|-----|
| Ala | Asp | Asn | Lys | Phe | Asn | Lys | Glu | Gln | Gln | Asn | Ala | Phe | Tyr |
| GAA | ATT | TTA | CAT | TTA | CCT | AAC | TTA | ACT | GAA | GAA | CAA | CGT | AAC |
| Glu | Ile | Leu | His | Leu | Pro | Asn | Leu | Thr | Glu | Glu | Gln | Arg | Asn |
| GGC | TTC | ATC | CAA | AGC | CTT | AAA | GAC | GAT | CCT | TCA | GTG | AGC | AAA |
| Gly | Phe | Ile | Gln | Ser | Leu | Lys | Asp | Asp | Pro | Ser | Val | Ser | Lys |
| GAA | ATT | TTA | GCA | GAA | GCT | AAA | AAG | CTA | AAC | GAT | GCT | CAA | GCA |
| Glu | Ile | Leu | Ala | Glu | Ala | Lys | Lys | Leu | Asn | Asp | Ala | Gln | Ala |
| CCA | AAA |     |     |     |     |     |     |     |     |     |     |     |     |
| Pro | Lys . |   |     |     |     |     |     |     |     |     |     |     |     |

27. A process for preparing a protein A material having domain E biological activity which comprises expression of cloned DNA, said cloned DNA comprising a nucleotide sequence coding for the amino acid sequence of domain E of said protein A material, and equivalent nucleotide sequences coding for molecules with substantially the same domain E biological activity, in a suitable microbial host, and recovering said protein A material; said nucleotide sequence and amino acid sequence are as follows:

| GCT | CAA | CAA | AAT | GCT | TTT | TAT | CAA | GTG | TTA | AAT | ATG | CCT | AAC |
|-----|-----|-----|-----|-----|-----|-----|-----|-----|-----|-----|-----|-----|-----|
| Ala | Gln | Gln | Asn | Ala | Phe | Tyr | Gln | Val | Leu | Asn | Met | Pro | Asn |
| TTA | AAC | GCT | GAT | CAA | CGT | AAT | GGT | TTT | ATC | CAA | AGC | CTT | AAA |
| Leu | Asn | Ala | Asp | Gln | Arg | Asn | Gly | Phe | Ile | Gln | Ser | Leu | Lys |
| GAT | GAT | CCA | AGC | CAA | AGT | GCT | AAC | GTT | TTA | GGT | GAA | GCT | CAA |
| Asp | Asp | Pro | Ser | Gln | Ser | Ala | Asn | Val | Leu | Gly | Glu | Ala | Gln |
| AAA | CTT | AAT | GAC | TCT | CAA | GCT | CCA | AAA |     |     |     |     |     |
| Lys | Leu | Asn | Asp | Ser | Gln | Ala | Pro | Lys . |   |     |     |     |     |

28. A process for preparing a protein A material having a protein A which comprises expression of cloned DNA, said cloned DNA comprising a nucleotide sequence coding for the amino acid sequence of the carboxy terminal domain of said protein A material, and equivalent nucleotide sequences coding for molecules with substantially the same biological activity, in a suitable microbial host, and recovering said protein A material; said nucleotide sequence and amino acid sequence are as follows:

| GAG | GAA | GAC | AAC | AAC | AAG | CCT | GGT | AAA | GAA | GAC | GGC | AAC | AAA |
|-----|-----|-----|-----|-----|-----|-----|-----|-----|-----|-----|-----|-----|-----|
| Glu | Glu | Asp | Asn | Asn | Lys | Pro | Gly | Lys | Glu | Asp | Gly | Asn | Lys |
| CCT | GGT | AAA | GAA | GAC | GGC | AAC | AAA | CCT | GGT | AAA | GAA | GAC | AAC |
| Pro | Gly | Lys | Glu | Asp | Gly | Asn | Lys | Pro | Gly | Lys | Glu | Asp | Asn |
| AAA | AAC | CTT | GGC | AAA | GAA | GAC | GGC | AAC | AAA | CCT | GGT | AAA | GAA |
| Lys | Asn | Leu | Gly | Lys | Glu | Asp | Gly | Asn | Lys | Pro | Gly | Lys | Glu |
| GAC | AAC | AAA | AAA | CCT | GGC | AAA | GAA | GAT | GGC | AAC | AAA | CCT | GGT |
| Asp | Asn | Lys | Lys | Pro | Gly | Lys | Glu | Asp | Gly | Asn | Lys | Pro | Gly |
| AAA | GAA | GAC | GGC | AAC | AAG | CCT | GGT | AAA | GAA | GAT | GGC | AAC | AAA |
| Lys | Glu | Asp | Gly | Asn | Lys | Pro | Gly | Lys | Glu | Asp | Gly | Asn | Lys |
| CCT | GGT | AAA | GAA | GAT | GGC | AAC | AAG | CCT | GGT | AAA | GAA | GAT | GGC |
| Pro | Gly | Lys | Glu | Asp | Gly | Asn | Lys | Pro | Gly | Lys | Glu | Asp | Gly |

-continued

| AAC | AAG | CCT | GGT | AAA | GAA | GAC | GGC | AAC | GGA | GTA | CAT | GTC | GTT |
|---|---|---|---|---|---|---|---|---|---|---|---|---|---|
| Asn | Lys | Pro | Gly | Lys | Glu | Asp | Gly | Asn | Gly | Val | His | Val | Val |
| AAA | CCT | GGT | GAT | ACA | GTA | AAT | GAC | ATT | GCA | AAA | GCA | AAC | GGC |
| Lys | Pro | Gly | Asp | Thr | Val | Asn | Asp | Ile | Ala | Lys | Ala | Asn | Gly |
| ACT | ACT | GCT | GAC | AAA | ATT | GCT | GCA | GAT | AAC | AAA | TTA | GCT | GAT |
| Thr | Thr | Ala | Asp | Lys | Ile | Ala | Ala | Asp | Asn | Lys | Leu | Ala | Asp |
| AAA | AAC | ATG | ATC | AAA | CCT | GGT | CAA | GAA | CTT | GTT | GTT | GAT | AAG |
| Lys | Asn | Met | Ile | Lys | Pro | Gly | Gln | Glu | Leu | Val | Val | Asp | Lys |
| AAG | CAA | CCA | GCA | AAC | CAT | GCA | GAT | GCT | AAC | AAA | GCT | CAA | GCA |
| Lys | Gln | Pro | Ala | Asn | His | Ala | Asp | Ala | Asn | Lys | Ala | Gln | Ala |
| TTA | CCA | GAA | ACT | GGT | GAA | GAA | AAT | CCA | TTC | ATC | GGT | ACA | ACT |
| Leu | Pro | Glu | Thr | Gly | Glu | Glu | Asn | Pro | Leu | Ile | Gly | Thr | Thr |
| GTA | TTT | GGT | GGA | TTA | TCA | TTA | GCG | TTA | GGT | GCA | GCG | TTA | TTA |
| Val | Phe | Gly | Gly | Leu | Ser | Leu | Ala | Leu | Gly | Ala | Ala | Leu | Leu |
| GCT | GGA | CGT | CGT | CGC | GAA | CTA | TAA |  |  |  |  |  |  |
| Ala | Gly | Arg | Arg | Arg | Glu | Leu | Stop. |  |  |  |  |  |  |

29. An essentially pure nucleotide sequence coding for the amino acid sequence of domain D, said nucleotide sequence and said amino acid sequence are as follows:

| GCT | GAC | AAC | AAT | TTC | AAC | AAA | GAA | CAA | CAA | AAT | GCT | TTC | TAT |
|---|---|---|---|---|---|---|---|---|---|---|---|---|---|
| Ala | Asp | Asn | Asn | Phe | Asn | Lys | Glu | Gln | Gln | Asn | Ala | Phe | Tyr |
| GAA | ATC | TTG | AAC | ATG | CCT | AAC | TTG | AAC | GAA | GAA | CAA | CGC | AAT |
| Glu | Ile | Leu | Asn | Met | Pro | Asn | Leu | Asn | Glu | Glu | Gln | Arg | Asn |
| GGT | TTC | ATC | CAA | AGC | TTA | AAA | GAT | GAC | CCA | AGT | CAA | AGT | GCT |
| Gly | Phe | Ile | Gln | Ser | Leu | Lys | Asp | Asp | Pro | Ser | Gln | Ser | Ala |
| AAC | CTT | TTA | GCA | GAA | GCT | AAA | AAG | TTA | AAT | GAA | TCT | CAA | GCA |
| Asn | Leu | Leu | Ala | Glu | Ala | Lys | Lys | Leu | Asn | Glu | Ser | Gln | Ala |
| CCG | AAA |  |  |  |  |  |  |  |  |  |  |  |  |
| Pro | Lys. |  |  |  |  |  |  |  |  |  |  |  |  | tide sequence and said amino acid sequence are as follows:

| GCT | GAT | GCG | CAA | CAA | AAT | AAG | TTC | AAC | AAA | GAT | CAA | CAA | AGC |
|---|---|---|---|---|---|---|---|---|---|---|---|---|---|
| Ala | Asp | Ala | Gln | Gln | Asn | Lys | Phe | Asn | Lys | Asp | Gln | Gln | Ser |
| GCC | TTC | TAT | GAA | ATC | TTG | AAC | ATG | CCT | AAC | TTA | AAC | GAG | GAG |
| Ala | Phe | Tyr | Glu | Ile | Leu | Asn | Met | Pro | Asn | Leu | Asn | Glu | Glu |
| CAA | CGC | AAT | GGT | TTC | ATT | CAA | AGT | CTT | AAA | GAC | GAT | CCA | AGC |
| Gln | Arg | Asn | Gly | Phe | Ile | Gln | Ser | Leu | Lys | Asp | Asp | Pro | Ser |
| CAA | AGC | ACT | AAC | GTT | TTA | GGT | GAA | GCT | AAA | AAA | TTA | AAC | GAA |
| Gln | Ser | Thr | Asn | Val | Leu | Gly | Glu | Ala | Lys | Lys | Leu | Asn | Glu |
| TCT | CAA | GCA | CCG | AAA |  |  |  |  |  |  |  |  |  |
| Ser | Gln | Ala | Pro | Lys. |  |  |  |  |  |  |  |  |  |

31. An essentially pure nucleotide sequence coding for the amino acid sequence of domain B, said nucleotide sequence and said amino acid sequence are as follows:

30. An essentially pure nucleotide sequence coding for the amino acid sequence of domain A, said nucleotide sequence and said amino acid sequence are as follows:

| GCT | GAT | AAC | AAA | TTC | AAC | AAA | GAA | CAA | CAA | AAT | GCT | TTC | TAT |
|---|---|---|---|---|---|---|---|---|---|---|---|---|---|
| Ala | Asp | Asn | Lys | Phe | Asn | Lys | Glu | Gln | Gln | Asn | Ala | Phe | Tyr |
| GAA | ATC | TTA | CAT | TTA | CCT | AAC | TTA | AAT | GAA | GAA | CAA | CGC | AAT |
| Glu | Ile | Leu | His | Leu | Pro | Asn | Leu | Asn | Glu | Glu | Gln | Arg | Asn |
| GGT | TTC | ATC | CAA | AGC | TTA | AAA | GAT | GAC | CCA | AGC | CAA | AGC | GCT |
| Gly | Phe | Ile | Gln | Ser | Leu | Lys | Asp | Asp | Pro | Ser | Gln | Ser | Ala |
| AAC | CTT | TTA | GCA | GAA | GCT | AAA | AAG | CTA | AAT | GAT | GCA | CAA | GCA |
| Asn | Leu | Leu | Ala | Glu | Ala | Lys | Lys | Leu | Asn | Asp | Ala | Gln | Ala |

| CCA | AAA |
|-----|-----|
| Pro | Lys |

32. An essentially pure nucleotide sequence coding for the amino acid sequence of domain C, said nucleotide sequence and said amino acid sequence are as follows:

| GCT | GAC | AAC | AAA | TTC | AAC | AAA | GAA | CAA | CAA | AAT | GCT | TTC | TAT |
|-----|-----|-----|-----|-----|-----|-----|-----|-----|-----|-----|-----|-----|-----|
| Ala | Asp | Asn | Lys | Phe | Asn | Lys | Glu | Gln | Gln | Asn | Ala | Phe | Tyr |
| GAA | ATT | TTA | CAT | TTA | CCT | AAC | TTA | ACT | GAA | GAA | CAA | CGT | AAC |
| Glu | Ile | Leu | His | Leu | Pro | Asn | Leu | Thr | Glu | Glu | Gln | Arg | Asn |
| GGC | TTC | ATC | CAA | AGC | CTT | AAA | GAC | GAT | CCT | TCA | GTG | AGC | AAA |
| Gly | Phe | Ile | Gln | Ser | Leu | Lys | Asp | Asp | Pro | Ser | Val | Ser | Lys |
| GAA | ATT | TTA | GCA | GAA | GCT | AAA | AAG | CTA | AAC | GAT | GCT | CAA | GCA |
| Glu | Ile | Leu | Ala | Glu | Ala | Lys | Lys | Leu | Asn | Asp | Ala | Gln | Ala |
| CCA | AAA | | | | | | | | | | | | |
| Pro | Lys | | | | | | | | | | | | |

33. A mixture of essentially pure nucleotide sequences coding for the amino acid sequence of domains D, or A, or B, or C of a protein A material having a protein A biological activity.

34. A mixture of essentially pure nucleotide sequences coding for the amino acid sequence of domain E of a protein A material having a protein A biological activity and domain D, or A, or B, or C, and equivalent nucleotide sequences coding for molecules with substantially the same protein A biological activity.

35. A recombinant DNA molecule comprising a nucleotide sequence encoding the amino acid sequence of a product selected from the group consisting of protein A, a polypeptide fragment thereof, and a mixture of polypeptide fragments thereof, each of said products having protein A biological activity.

36. A recombinant DNA molecule of claim 35 encoding the amino acid sequence of a polypeptide fragment of protein A.

37. A recombinant DNA molecule of claim 35 encoding the amino acid sequence of protein A.

38. An essentially pure DNA molecule consisting essentially of a nucleotide sequence encoding the amino acid sequence of a product selected from the group consisting of protein A, a polypeptide fragment thereof, and a mixture of polypeptide fragments thereof, each of said products having protein A biological activity.

39. A recombinant DNA vector containing a DNA molecule comprising a nucleotide sequence encoding the amino acid sequence of a product selected from the group consisting of protein A, a polypeptide fragment thereof, and a mixture of polypeptide fragments thereof, each of said products having protein A biological activity.

40. A microorganism containing a recombinant DNA vector of claim 39.

41. A microorganism of claim 40 wherein said DNA molecule is derived from staphylococcal bacteria.

42. A microorganism of claim 41 wherein said bacteria comprises *Staphylococcus aureus*.

43. A microorganism of claim 42 wherein said DNA molecule additionally includes 5' regulatory sequences and the ribosome binding site of the protein A gene, said 5' regulatory sequences and ribosome binding site being derived from *Staphylococcus aureus*.

44. A microorganism of claim 43 comprising *E. coli*.

45. A recombinant DNA molecule comprising the following nucleotide sequence encoding protein A material.

* * * * *

UNITED STATES PATENT AND TRADEMARK OFFICE
CERTIFICATE OF CORRECTION

PATENT NO. : 5,151,350

DATED : September 29, 1992

INVENTOR(S) : Donald A. Colbert and Algis Anilionis

It is certified that error appears in the above-identified patent and that said Letters Patent is hereby corrected as shown below:

Column 17, Claim 5, line 1, cancel "claim 6" and insert therefor --claim 4--;

Column 18, Claim 6, line 1, cancel "vecvtor" and insert therefor --vector--;

Signed and Sealed this

Twenty-eighth Day of December, 1993

Attest:

*Attesting Officer*

BRUCE LEHMAN

*Commissioner of Patents and Trademarks*